(12) United States Patent
Bright

(10) Patent No.: US 6,525,048 B1
(45) Date of Patent: Feb. 25, 2003

(54) AZABICYCLIC 5HT1 RECEPTOR LIGANDS

(75) Inventor: Gene Michael Bright, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/403,892

(22) PCT Filed: Mar. 18, 1999

(86) PCT No.: PCT/IB99/00457
§ 371 (c)(1),
(2), (4) Date: Jan. 18, 2000

(87) PCT Pub. No.: WO99/52907
PCT Pub. Date: Oct. 21, 1999

Related U.S. Application Data

(60) Provisional application No. 60/081,237, filed on Apr. 9, 1998.

(51) Int. Cl.[7] ............... A61K 31/5377; A61K 31/4985; C07D 471/04
(52) U.S. Cl. .................. 514/233.2; 514/249; 544/116; 544/119; 544/349
(58) Field of Search ................. 544/349, 116, 544/119; 514/249, 233.2

(56) References Cited

U.S. PATENT DOCUMENTS

| | | | |
|---|---|---|---|
| 5,106,849 A | * | 4/1992 | Abou-Gharbia et al. |
| 5,122,525 A | * | 6/1992 | Bright et al. |
| 5,157,034 A | * | 10/1992 | Bright et al. ............ 544/349 |
| 5,565,453 A | * | 10/1996 | Bright et al. |
| 5,614,523 A | * | 3/1997 | Audia et al. |
| 5,719,286 A | * | 2/1998 | Urban |
| 5,731,307 A | * | 3/1998 | Desai |
| 6,008,227 A | * | 12/1999 | Davies et al. |

FOREIGN PATENT DOCUMENTS

| WO | WO9215580 | 9/1992 |
|---|---|---|
| WO | 95/31988 | * 11/1995 |

OTHER PUBLICATIONS

Robichaud et al., Annual Reports in Medicinal Chemistry, vol. 35, p. 11–20 (2000).*

* cited by examiner

*Primary Examiner*—Emily Bernhardt
(74) *Attorney, Agent, or Firm*—P. C. Richardson; P. H. Ginsburg; A. D. Joran

(57) ABSTRACT

The present invention relates to compounds of the formula

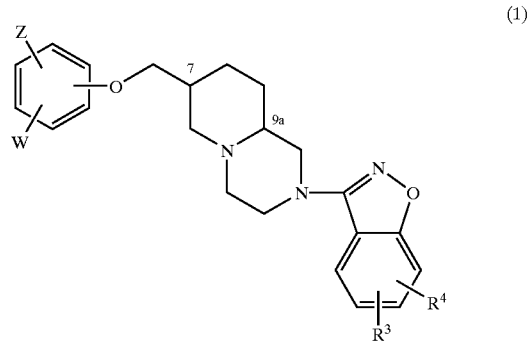

(1)

These compounds are useful as psychotherapeutic agents.

3 Claims, No Drawings

AZABICYCLIC 5HT1 RECEPTOR LIGANDS

The present application is the U.S. national stage Section 371 of International patent application No. PCT/IB99/00457, filed Mar. 18, 1999, which claims priority from U.S. provisional application Ser. No. 60/081,237, filed Apr. 9, 1998.

BACKGROUND OF THE INVENTION

The present invention relates to novel aminomethylphenoxymethyl/benzisoxazole substituted azabicyclic compounds, to intermediates for their preparation, to pharmaceutical compositions containing them and to their medicinal use. The compounds of the present invention include selective agonists and antagonists of serotonin 1 (5-HT1) receptors, specifically, of one or both of the 5-HT1A and 5-HT1D receptors. They are useful in treating or preventing migraine, depression and other disorders for which a 5-HT1 agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-HT1 agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4-substituted-piper-azinyl)-naphthalenes as useful 5-HT1A ligand therapeutics.

PCT publication WO 94/21619, published Sep. 29, 1994, refers to naphthalene derivatives as 5-HT1 agonists and antagonists.

PCT publication WO 96/00720, published Jan. 11, 1996, refers to naphthyl ethers as useful 5-HT1 agonists and antagonists.

European Patent Publication 701,819, published Mar. 20, 1996, refers to the use of 5-HT1 agonists and antagonists in combination with a 5-HT re-uptake inhibitor.

Glennon et al., refers to 7-methoxy-1-(1-piperazinyl)-naphthalene as a useful 5-HT1 ligand in their article "5-HT1D Serotonin Receptors", *Clinical Drug Res. Dev.*, 22, 25–36 (1991).

Glennon's article "Serotonin Receptors: Clinical Implications", *Neurscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

World Patent Application WO 95/31988, published Nov. 30, 1995, refers to the use of a 5-HT1D antagonist in combination with a 5-HT1A antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura et al., *J. Neurochem*, 66 (1), 203–209 (1996), have stated that administration of agonists selective for 5-HT1A receptors or for both 5-HT1A and 5-HT1D receptors might represent a great improvement in the treatment of human cerebellar ataxias, a muflifaceted syndrome for which no established therapy is available.

European Patent Publication 666,261, published Aug. 9, 1995 refers to thiazine and thiomorpholine derivatives which are claimed to be useful for the treatment of cataracts.

SUMMARY OF THE INVENTION

The present invention relates to compounds of the formula

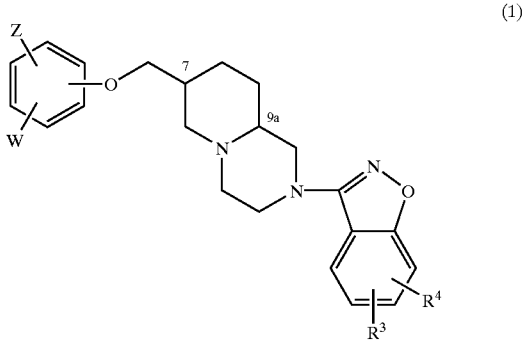

wherein
$R^3$, $R^4$, and Z are selected, independently, from hydrogen, halo (e.g., chloro, fluoro, bromo or iodo), $(C_1-C_4)$ alkyl optionally substituted with from one to three fluorine atoms, $(C_1-C_4)$alkoxy optionally substituted with from one to three fluorine atoms, and $(C_1-C_4)$alkoxy-$(C_1-C_4)$alkyl wherein each of the alkyl moieties may optionally be substituted with from one to three fluorine atoms;

W is —$CH_2$—O—$(C_1-C_6)$ alkyl wherein the alkyl moiety can be straight or branched;

or W is —$CH_2NR^1R^2$ wherein $R^1$ and $R^2$ are independently selected from hydrogen and straight or branched $(C_1-C_6)$alkyl;

or $R^1$ and $R^2$, together with the nitrogen to which they are attached, form a saturated four membered monocyclic ring or a saturated or unsaturated nonaromatic five to seven membered monocyclic ring or a saturated or unsaturated nonaromatic seven to ten membered bicyclic ring which may optionally contain one or two heteroatoms in addition to the nitrogen of $NR^1R^2$, wherein said heteroatoms are independently selected from oxygen, nitrogen and sulfur, and wherein from one to three of the ring carbon atoms, or one of the ring nitrogen atoms, may optionally and independently be substituted with straight or branched $(C_1-C_4)$ alkyl, straight or branched $(C_1-CG)$ alkoxy, straight or branched $(C_1-C_3)$ alkyl($C_3-C_7$) cycloalkyl, hydroxy, amino, cyano, halo, aryl-(straight or branched $(C_1-C_3)$ alkyl) or heteroaryl-(straight or branched $(C_1-C_3)$ alkyl), wherein said aryl is selected from phenyl and naphthyl and said heteroaryl is selected from oxazolyl, isoxazoyl, thiazolyl, isothiazolyl, furanyl, pyrazolyl, pyrrolyl, tetrazolyl, triazolyl, thienyl, imidazolyl, pyrazinyl, pyrazolyl, indolyl, isoindolyl, pyrazinyl, cinnolinyl, pyridinyl and pyrimidinyl;

with the proviso that in any ring formed by $NR^1R^2$: (a) there can be -no more than one ring oxygen atom; (b) there can be no hydroxy, alkoxy, alkoxyalkyl, cyano, amino or alkylamino moiety bonded directly to any ring nitrogen atom; and (c) no ring carbon that is double bonded to another ring carbon and not part of an aromatic ring system can be bonded to a ring oxygen atom or ring nitrogen atom.

Examples of preferred compounds of the formula I are those having the absolute stereochemical configuration defined as 7R, 9aS -trans or as 7S, 9aS -cis.

Examples of specific embodiments of this invention are the following compounds of the formula I and their pharmaceutically acceptable salts:

(7R,9aS)-trans-1-{3-[2-(5-Fluoro-benzo[d]isoxazol-3-yl)-octahydropyrido[1,2-a]pyrazin-7-ylmethoxy]-benzyl}-azetidin-3-ol;

(7R,9aS)-trans-2-(5-Fluoro-benzo[d]isoxazol-3-y)-7-(3-morpholin-4-ylmethylphenoxymethyl)-octahydro-pyrido[1,2-a]pyrazine;

(7S,9aS)-cis-1-(3-{1-[2-(Benzo[d]isoxazol-3-yl-methyl-amino)-ethyl]-6-methyl-piperidin-3-ylmethoxy}-benzyl)-azetidin-3-ol;

(7R,9aS)-trans-2-(4-Fluoro-benzo[d]isoxazol-3-yl)-7-(3-pyrrolidin-1-ylmethyl-phenoxymethyl)-octahydro-pyrido[1,2-a]pyrazine;

(7S,9aS)-cis-2-Benzo[d]isoxazol-3-yl-7-(3-pyrrolidin-1-ylmethyl-phenoxymethyl)-octahydro-pyrido-[1,2-a]pyrazine;

(7S,9aS)-cis-1-[3-(2-Benzo[d]isoxazol-3-yl-octahydro-pyrido[1,2-a]pyrazin-7-ylmethoxy)-benzyl]pyrrolidine-3,4-diol;

(7R,9aS)-trans-2-(5-Fluoro-benzo[d]isoxazol-3-yl)-7-(3-pyrrolidin-1-ylmethyl-phenoxymethyl)-octahydropyrido[1,2-a]pyrazine;

(7S,9aS)-cis-2-Benzo[d]isoxazol-3-yl-7-(2-methyl-5-pyrrolidin-1-ylmethyl-phenoxymethyl)-octahydro-pyrido[1,2-a]pyrazine;

(7S,9aS)-cis-2-Benzo[d]isoxazol-3-yl-7-(3-methoxy-5-pyrrolidin-1-ylmethyl-phenoxymethyl)-octahydro-pyrido[1,2-a]pyrazine;

(7S,9aS)-cis-2-Benzo[d]isoxazol-3-yl-7-(4-chloro-3-pyrrolidin-1-ylmethyl-phenoxymethyl)-octahydro-pyrido[1,2-a]pyrazine;

(7S,9aS)-cis-2-Benzo[d]isoxazol-3-yl-7-(4-pyrrolidin-1-ylmethyl-phenoxymethyl)-octahydro-pyrido[1,2-a]pyrazine;

(7S,9aS)-cis-7-(3-azetidin-1-ylmethyl-phenoxymethyl)-2-benzo[d]isoxazol-3-yl-octahydro-pyrido[1,2-a]pyrazine;

(7S,9aS)-cis-[3-(2-Benzo[d]isoxazol-3-yl-octahydro-pyrido[1,2-a]pyrazin-7-ylmethoxy)-benzyl]-cyclopropylmethyl-amine;

(7S,9aS)-cis-2-Benzo[d]isoxazol-3-yl-7-[3-(2-methoxymethyl-pyrrolidin-1-ylmethyl)-phenoxymethyl]-octahydro-pyrido[1,2-a]pyrazine;

(7S,9aS)-cis-[3-(2-Benzo[d]isoxazol-3-yl-octahydro-pyrido[1,2-a]pyrazin-7-ylmethoxy)-benzyl]-cyclopropyl-amine;

(7S,9aS)-cis-2-Benzo[d]isoxazol-3-yl-7-(3-pyrrolidin-1-ylmethyl-phenoxymethyl)-octahydro-pyridol[1,2-a]pyrazine;

(7S,9aS)-cis-2-Benzo[d]isoxazol-3-yl-7-[3-(4-ethyl-piperazin-1-ylmethyl)-phenoxymethyl]-octahydro-pyrido[1,2-a]pyrazine;

(7S,9aS)-cis-[3-(2-Benzo[d]isoxazol-3-yl-octahydro-pyrido[1,2-a]pyrazin-7-ylmethoxy)-benzyl]-cyclohexyl-amine;

(7S,9aS)-cis-1-[3-(2-Benzo[d]isoxazol-3-yl-octahydro-pyridol[1,2-a]pyrazin-7-ylmethoxy)-benzyl]-pyrrolidin-3-ol;

(7S,9aS)-cis-2-Benzo[d]isoxazol-3-yl-7-[3-(2,5-dimethyl-[pyrrolidin-1-ylmethyl)-phenoxymethyl-octahydro-pyrido[1,2-a]pyrazine;

(7S,9aS)-cis-2-Benzo[d]isoxazol-3-yl-7-[3-(2,5-dimethyl-pyrrolidin-1-ylmethyl)-phenoxymethyl]-octahydro-pyridol[1,2-a]pyrazine;

(7S,9aS)-cis-1-[3-(2-Benzo[d]isoxazol-3-yl-octahydro-pyrido[1,2-a]pyrazin-7-ylmethoxy)-benzyl]-pyrrolidine-3,4-diol;

(7S,9aS)-cis-1-[3-(2-Benzo[d]isoxazol-3-yl-octahydro-pyrido[1,2-a]pyrazin-7-ylmethoxy)-benzyl]-pyrrolidin-3-ol;

(7S,9aS)-cis-[3-(2-Benzo[d]isoxazol-3-yl-octahydro-pyrido[1,2-a]pyrazin-7-ylmethoxy)-benzyl]-isobutyl-amine;

(7S,9aS)-cis-Benzo[d]isoxazol-3-yl-methyl-{2-[2-methyl-5-(2-morpholin-4-methyl-phenoxymethyl)-piperidin-1-yl]-ethyl}-amine;

(7S ,9aS)-cis-2-Benzo[d]isoxazol-3-yl-7-(2-pyrrolidin-1-ylmethyl-phenoxymethyl)-octahydro-pyridol[1,2-a]pyrazine;

(7S ,9aS)-cis-2-Benzo[d]isoxazol-3-yl-7-(4-morpholin-4-ylmethyl-phenoxymethyl)-octahydro-pyrido[1,2-a]pyrazine;

(7S,9aS)-cis-2-Benzo[d]isoxazol-3-yl-7-(4-pyrrolidin-1-ylmethyl -phenoxymethyl)-octahydro-pyridol[1,2-a]pyrazine;

(7R,9aS)]-trans-2-(7-Fluoro-benzo[d]isoxazol-3-yl)-7-3-pyrrolidin-1-ylmethyl-phenoxymethyl)-octahydro-pyrido[1,2-a]pyrazine;

(7R,9aS)-trans-2-(6Fluoro-benzo[d]isoxazol-3-yl)-7-(3-pyrrolidin-1-ylmethyl-phenoxymethyl)-octahydro-pyrido[1,2-a]pyrazine;

(7R,9aS)-trans-2-(6,7-Difluoro-benzodisoxazol-3-yl)-7-(3-pyrrolidin-1-ylmethyl-phenoxymethyl)-octahydro-pyrido[1,2-a]pyrazine;

(7R,9aS)-trans-3-(3-[2-(5-Fluoro-benzo[d]isoxazol-3-yl)-octahydro-pyrido[1,2-a]pyrazin-7-ylmethoxy]-benzyl)-3-aza-bicyclo[3,2,2]nonane and;

(7R,9aS)-trans-2-(5-Fluoro-benzo[d]isoxazol-3-yl)-7-[3-Cis-octahydro-isoindol-2-ylmethyl)-phenoxymethyl]-octahydro-pyrido[1,2-a]pyrazine.

Other specific embodiments of this invention are the following compounds of the formula I and their pharmaceutically acceptable salts:

(7S,9aS)-trans-2-(5-Fluoro-benzo[d]isoxazol-3-yl)-7-(2-pyrrolidin-1-ylmethyl-phenoxymethyl)-octahydro-pyrido[1,2-a]pyrazine;

(7S,9aS)-trans-2-(5-Chloro-benzo[d]isoxazol-3-yl)-7-(3-pyrrolidin-1-ylmethyl-phenoxymethyl)-octahydro-pyrido[1,2-a]pyrazine;

(7S,9aS)-trans-2-(5-Methyl-benzo[d]isoxazol-3-yl)-7-(3-pyrrolidin-1-ylmethyl-phenoxymethyl)-octahydro-pyrido[1,2-a]pyrazine;

(7S,9aS)-trans-2-Benzo[d]isoxazol-3-yl)-7-(2-pyrrolidin-1-ylmethyl-phenoxymethyl)-octahydro-pyrido[1,2-a]pyrazine;

(7R,9aS)-cis-2-Benzo[d]isoxazol-3-yl)-7-(2-pyrrolidin-1-ylmethyl-phenoxymethyl)-octahydro-pyrido[1,2-a]pyrazine;

(7S,9aS)-trans-2-(5-Fluoro-benzo[d]isoxazol-3-yl)-7-(2-morpholin-4-ylmethyl-phenoxymethyl)-octahydro-pyrido[1,2-a]pyrazine;

(7S,9aS)-trans-2-(5-Fluoro-benzo[d]isoxazol-3-yl)-7-(4-morpholin-4-ylmethyl-phenoxymethyl)-octahydro-pyrido[1,2-a]pyrazine;

(7R,9aS)-trans-2-(2-Methoxy-benzo[d]isoxazol-3-yl)-7-(3-pyrrolidin-1-ylmethyl-phenoxymethyl)-octahydro-pyrido[1,2-a]pyrazine;

(7S,9aS)-cis-2-(5-Methoxy-benzo[d]isoxazol-3yl-7-(3-pyrrolidin-1-ylmethyl-phenoxymethyl)-octahydro-pyrido[1,2-a]pyrazine;

(7R,9aS)-trans-2-(5-Fluoro-benzo[d]isoxazol-3-yl)-7-(3-(2-methoxymethyl-pyrrolidin-1-ylmethyl-phenoxymethyl)-octahydro-pyrdo[1,2-a]pyrazine;

(7R,9aS)-trans-2-(5-Fluoro-benzo[d]isoxazol-3-yl)-7-[3-(2-methoxymethyl-pyrrolidin-1-ylmethyl-phenoxymethyl)-octahydro-pyrido[1,2-a]pyrazine;

(7R,9aS)-tans-2-(5-Fluoro-benzo[d]isoxazol-3-yl)-7-[3-(2-methoxymethyl-piperidin1-ylmethyl-phenoxymethyl)-octahydro-pyrido[1,2-a]pyrazine; and (7R,9aS)-trans-2-(5-Fluoro-benzo[d]isoxazol-3-yl)-7-[3-(3-methoxymethyl-piperidin-1-ylmethyl)-phenoxymethyl]-octahydro-pyrido[1,2-a].

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising an amount of a compound of the formula I or a pharmaceutically acceptable salt thereof effective in treating such disorder or condition and a pharmaceutically acceptable carrier.

The present invention also relates to a pharmaceutical composition for treating a disorder or condition that can be treated by modulating serotonergic neurotransmission in a mammal, preferably a human, comprising an amount of a compound of the formula I, or a pharmaceutically acceptable salt thereof, effective in treating such disorder or condition and a pharmaceutically acceptable carrier. Examples of such disorders and conditions are those enumerated in the preceding paragraph.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (, agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g, addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer, (e.g., small cell lung carcinoma), chronic paroxysmal hemicrania and headache (associated with vascular disorders) in a mammal, preferably a human, comprising administering to a mammal in need of such treatment an amount of a compound of the formula I, or a pharmaceutically acceptable salt thereof, that is effective in treating such disorder or condition.

The present invention also relates to a method for treating a disorder or condition that can be treated by modulating serotonergic neurotransmission in a mammal, preferably a human, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive dedine (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising a serotonin 1A receptor antagonizing or agonizing effective amount, or a serotonin 1D receptor antagonizing effective amount, of a compound of the formula I, or a pharmaceutically acceptable salt thereof, and a pharmaceutically acceptable carrier.

The present invention also relates to a pharmaceutical composition for treating a disorder or condition that can be treated by modulating serotonergic neurotransmission in a mammal, preferably a human, comprising a serotonin 1A receptor antagonizing or agonizing effective amount, or a serotonin 1D receptor antagonizing effective amount, of a compound of the formula I, or a pharmaceutically acceptable salt thereof, and a pharmaceutically acceptable carrier.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising administering to a mammal requiring such treatment a serotoninn 1A receptor antagonizing or agonizing effective amount, or a serotonin 1D receptor antagonizing effective amount, of a compound of the formula I or a pharmaceutically acceptable salt thereof.

The present invention also relates to a method for treating a disorder or condition that can be treated by modulating serotonergic neurotransmission in a mammal, preferably a human, comprising administering to a mammal requiring such treatment a serotonin 1A receptor antagonizing or agonizing effective amount, or a serotonin 1D receptor antagonizing effective amount, of a compound of the formula I or a pharmaceutically acceptable salt thereof.

The present invention relates to a pharmaceutical composition for treating a condition or disorder that can be treated by modulating serotonergic neurotransmission in a mammal, preferably a human, comprising:
  a) a pharmaceutically acceptable carrier;
  b) a compound of the formula I or a pharmaceutically acceptable salt thereof; and
  c) a 5-HT re-uptake inhibitor, preferably sertraline, or a pharmaceutically acceptable salt thereof;
  wherein the amount of the active compounds (i.e., the compound of formula I and the 5-HT re-uptake inhibitor) are such that the combination is effective in treating such disorder or condition.

The present invention also relates to a method for treating a disorder or condition that can be treated by modulating serotonergic neurotransmission in a mammal, preferably a human, comprising administering to a mammal requiring such treatment:
  a) a compound of the formula I, defined above, or a pharmaceutically acceptable salt thereof; and
  b) a 5-HT re-uptake inhibitor, preferably sertraline, or a pharmaceutically acceptable salt thereof;
  wherein the amounts of the active compounds (i.e., the compound of formula I and the 5-HT re-uptake inhibitor) are such that the combination is effective in treating such disorder or condition.

The present invention also relates to a method for treating a disorder or condition that can be treated by modulating serotonergic neurotransmission in a mammal, preferably a human, comprising administering to said mammal requiring such treatment:
  a) a 5-HT1A agonist or antagonist or a pharmaceutically acceptable salt thereof; and
  b) a 5-HT1D antagonist of formula I or a pharmaceutically acceptable salt thereof:
  wherein the amounts of each active compound (i.e., the 5-HT1A agonist or antagonist and the 5-HT1D antagonist) are such that the combination is effective in treating such disorder or condition.

The present invention also relates to a pharmaceutical composition for treating a disorder or condition that can be treated by modulating serotonergic neurotransmission in a mammal, preferably a human, comprising:
  a) a 5-HT1A agonist or antagonist or a pharmaceutically acceptable salt thereof; and
  b) a 5-HT1D antagonist of formula I or a pharmaceutically acceptable salt thereof;
  wherein the amounts of each active compound (i.e., the 5-HT1A agonist or antagonist and the 5-HT1D antagonist) are such that the combination is effective in treating such disorder or condition.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

The present invention also relates to all radiolabelled forms of the compounds of the formula I. Preferred radiolabelled compounds of formula I are those wherein the radiolabels are selected from as $^3$H, $^{11}$C, $^{14}$C, $^{18}$F, $^{123}$I and $^{125}$I. Such radiolabelled compounds are useful as research and diagnostic tools in metabolism pharmacokinetics studies and in binding assays in both animals and man.

"Modulating serotonergic neurotransmission," as used herein, refers to increasing or improving, or decreasing or retarding the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbartitol, and benzodiazepines (e.g., Valium (trademark)). "Treating a chemical dependency," as used herein, means reducing or alleviating such dependency.

Sertraline, (1S-cis)-4-(3,4-dichlorophenyl)-1,2,3,4-tetrahydro-N-methyl-1-naphthalenamine, as used herein has the chemical formula $C_{17}H_{17}NCl_2$ and the following structural formula

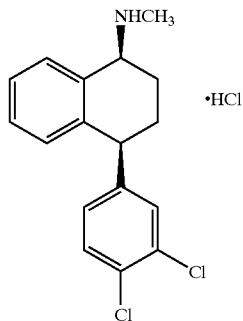

Its synthesis is described in U.S. Pat. No. 4,536,518. assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

This invention also relates to compounds of the formula

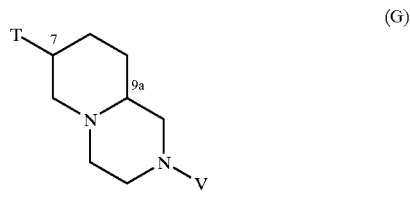

(G)

wherein the stereochemistry is either (7R, 9aS)-trans or (7S, 9aS)-cis;

T is selected from $HOCH_2-$, $HC(=O)-$, $H_3CO_2SOCH_2-$, $-CH_2NR^1R^2$, straight or branched $(C_1-C_6)$alkoxy, and

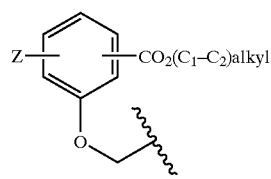

wherein

Z is defined as in the definition of compounds of the formula I; and

V is selected from hydrogen, t-butoxycarbonyl, groups having the formula

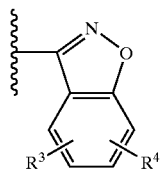

wherein $R^3$ and $R^4$ are selected, independently, from hydrogen, chloro, fluoro, methyl and methoxy, and groups having the formula

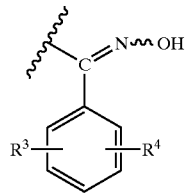

wherein $R^3$ and $R^4$ are defined as above and the oximino moiety may be syn, anti, or a mixture of syn and anti isomers.

Such compounds are useful in the synthesis of compounds of the formula I.

Examples of specific compounds of the formula G are the following:

7R,9aS)-trans-7-(3-methoxycarbonylphenoxymethyl)-octahydro-pyrido-1,2-a]pyrazine-2-carboxylic acid tert-butyl ester;

(7R,9aS)-trans-7-(3-hydroxymethylphenoxymethyl)-octahydro-pyrido-[1,2-a]pyrazine-2-carboxylic acid tert-butyl ester;

(7R,9aS)-trans-7-(3-pyrrolidin-1-ylmethyl-phenoxymethyl)-octahydro-pyrido[1,2-a]pyrazine-2-carboxylic acid tert-butyl ester;

(7R,9aS)-trans-3-(3-pyrrolidin-1-ylmethyl-phenoxymethyl)-octahydro-quinazolizine dihydrochloride and mineral bis-salts thereof;

(7R,9aS)-trans-[2-(5-fluoro-benzo[d]isoxazol-3-yl)-octahydro-pyrido-1,2-a]pyrazin-7-yl]-methanol;

(7S,9aS)-trans-3-[2-(fluoro-benzo[d]isoxazol-3-yl)-octahydro-pyrido[1,2-a]pyrazin-7-ylmethoxy]-benzoic acid methyl ester;

(7R,9aS)-trans-{3-[2-(5-fluoro-benzo[d]isoxazol-3-yl)-octahydro-pyrido[1,2-a]pyrazin-7-ylmethoxy]-phenyl}-methanol;

(7R,9aS)-trans-{3-[2-(5-fluoro-benzo[d]isoxazol-3-yl)-octahydro-pyrido[1,2-a]pyrazin-7-ylmethoxy]-phenyl}-methanol methane sulfonate;

(7S,9aS)-cis-7-(3-methoxycarbonyl-phenoxymethyl)-octahydro-pyrido[1,2-a]pyrazine-2-carboxylic acid tert-butyl ester;

(7S,9aS)-cis-{2-[5-(3-hydroxymethyl-phenoxymethyl)-2-methyl-piperidin-1-yl]ethyl}-methyl-carbamic acid tert-butyl ester;

(7S,9aS)-cis-3-(2-Benzo[d]isoxazol-3-yl-octahydro-pyrido[1,2-a]pyrazin-7-ylmethoxy)-benzoic acid methyl ester;

(7S,9aS)-cis-[3-(2-Benzo[d]isoxazol-3-yl-octahydro-pyrido[1,2-a]pyrazin-7-ylmethoxy)-phenyl]-methanol;

(7S,9aS)-cis-4-(2-Benzo[d]isoxazol-3-yl-octahydro-pyrido[1,2-a]pyrazin-7-ylmethoxy)-benzoic acid methyl ester;

(7S,9aS)-cis-[4-(2-Benzo[d]isoxazol-3-yl-octahydro-pyrido[1,2-a]pyrazin-7-ylmethoxy)phenyl]-methanol;

(7S,9aS)-cis-2-Benzo[d]isoxazol-3-yl-7-(4-chloromethyl-phenoxymethyl)-octahydro-pyrido[1,2-a]pyrazine;

(7S,9aS)-cis-2-{1-[2-(Benzo[d]isoxazol-3-yl-methyl-amino)-ethyl]-6-methyl-piperidin-3-ylmethoxy}-benzonitrile;

(7S,9aS)-{2-[5-(2-Aminomethyl-phenoxymethyl)-2-methyl-piperidin-1-yl]-ethyl}-benzo[d]isoxazol-3-yl-methyl-amine;

(7S,9aS)-cis-4-(2-Benzo[d]isoxazol-3-yl-octahydro-pyrido[1,2-a]pyrazin-7-ylmethoxy)-benzonitrile;

(7S,9aS)-cis-4-(2-Benzo[d]isoxazol-3-yl-octahydro-pyrido-1,2-a]pyrazin-7-ylmethoxy)-benzylamine;

(7S,9aS)-cis-[2-(5-fluoro-benzo[d]isoxazol-3-yl)-octahydro-pyrido[1,2-a]pyrazin-7-yl]-methanol;

(7S,9aS)-cis-2-(5-fluoro-benzo[d]isoxazol-3-yl)-octahydro-pyridol[1,2-a]pyrazine-7-carboxaldehyde;

(7R,9aS)-trans-2-(5-fluoro-benzo[d]isoxazol-3-y)-octahydro-pyridol[1,2-a]pyrazin-7-carboxaldehyde;

(7R,9aS)-trans-[2-(5-fluoro-benzo[d]isoxazol-3-yl)-octahydro-pyridol[1,2-a]pyrazin-7-yl]-methanol and; and (7R,9aS)-trans-methanesulfonic acid-2-(5-fluoro-benzo[d]isoxazol-3-yl)-octahydro-pyridol[1,2-a]pyrazin-7-yl-ester.

DETAILED DESCRIPTION OF THE INVENTION

Compounds of the formula I may be prepared according to the following reaction schemes and discussion. Unless otherwise indicated, W, Z, T, V, $R^1$, $R^2$, $R^3$ and $R^4$ and structural formulas I and G in the reaction schemes and discussion that follow are as defined above.

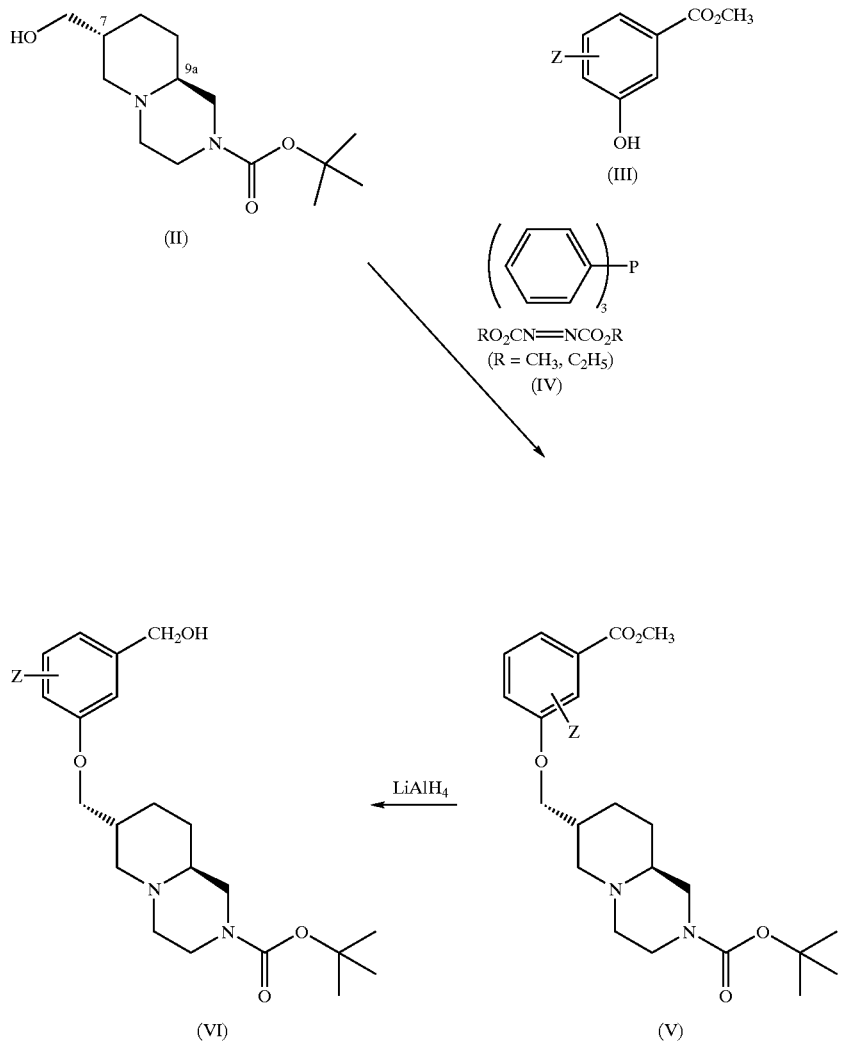

SCHEME 1

-continued
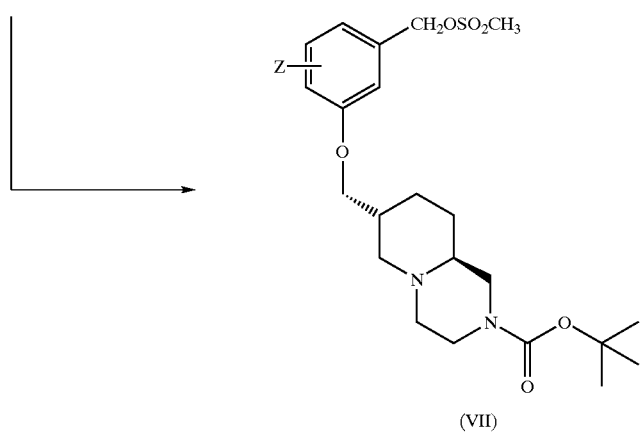
(VII)
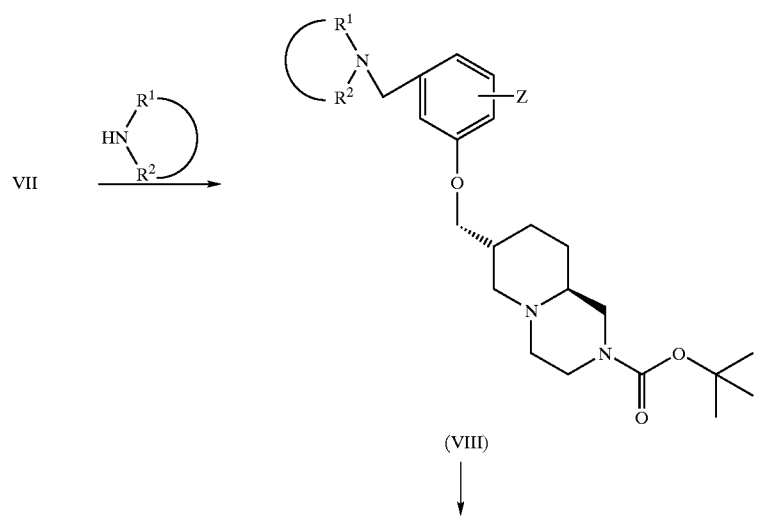
(VIII)
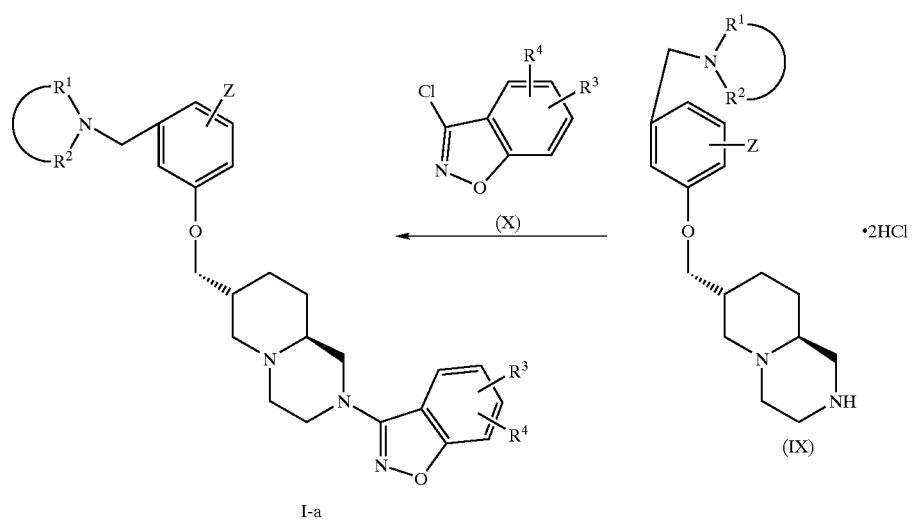

SCHEME 2
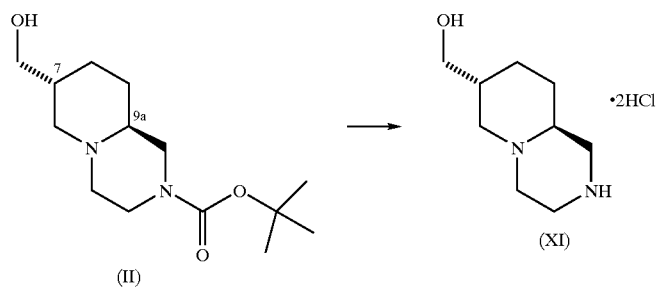
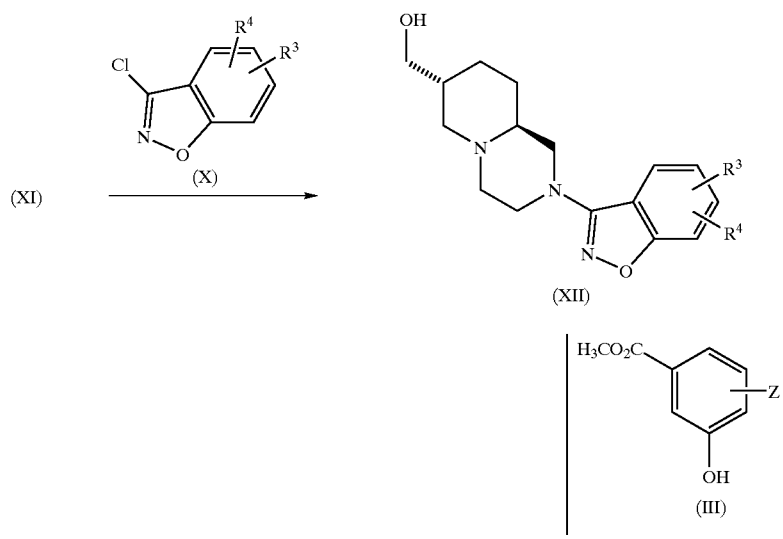
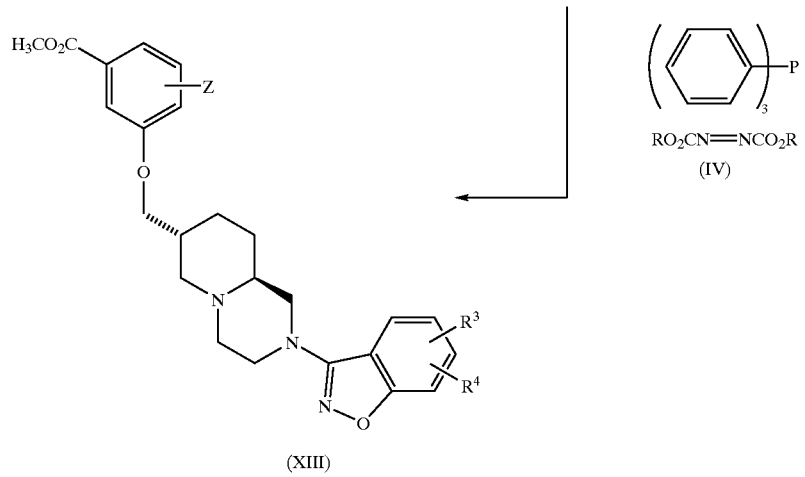

-continued
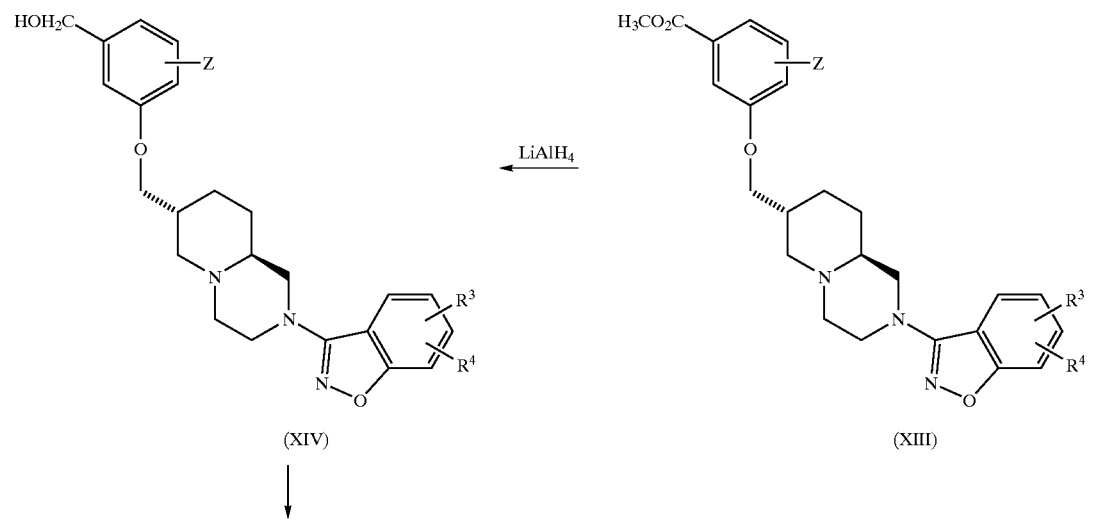
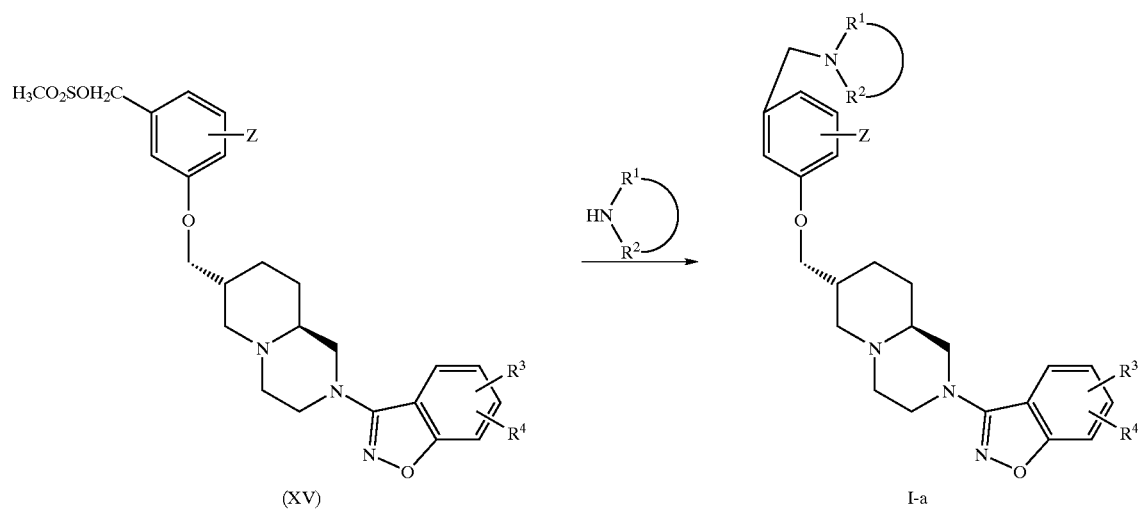
SCHEME 3
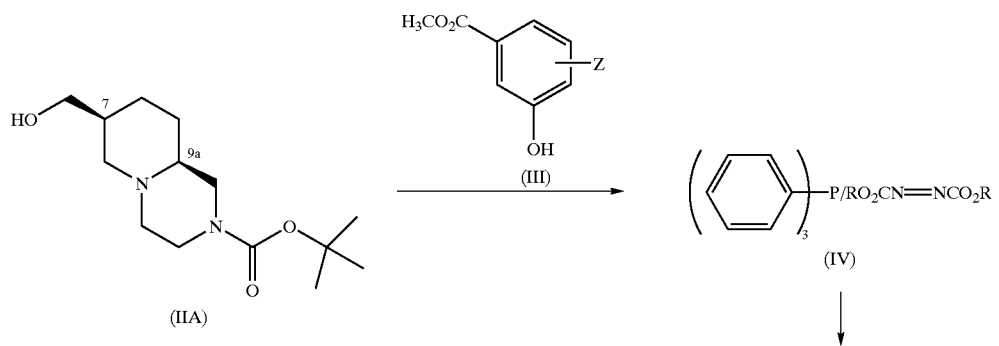

-continued
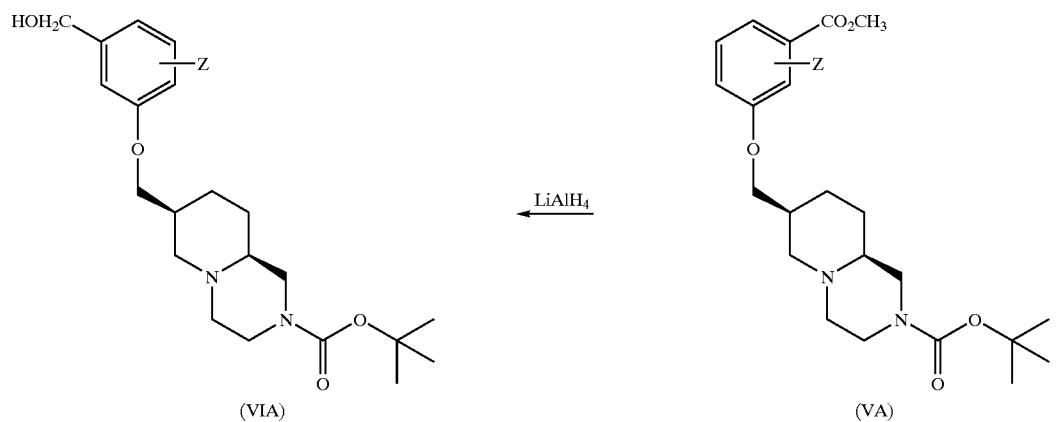
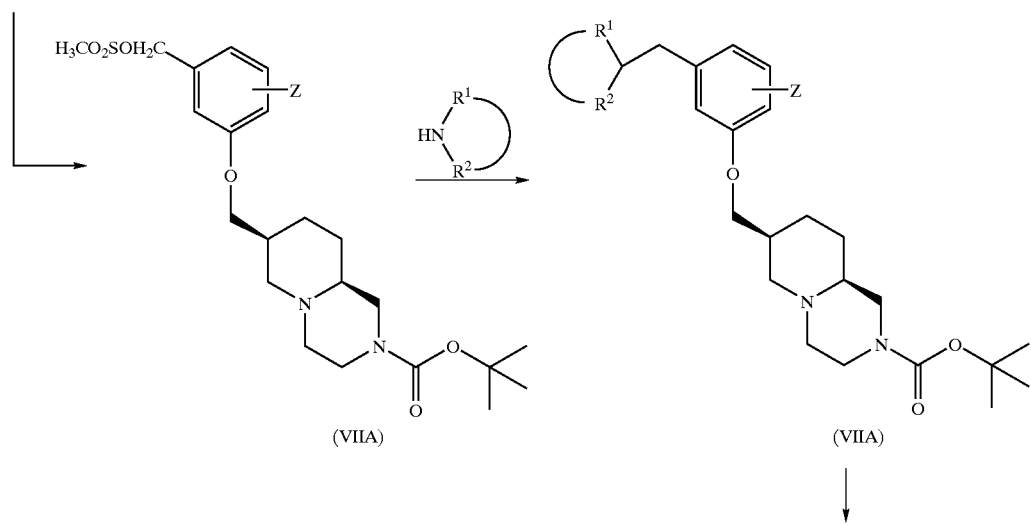
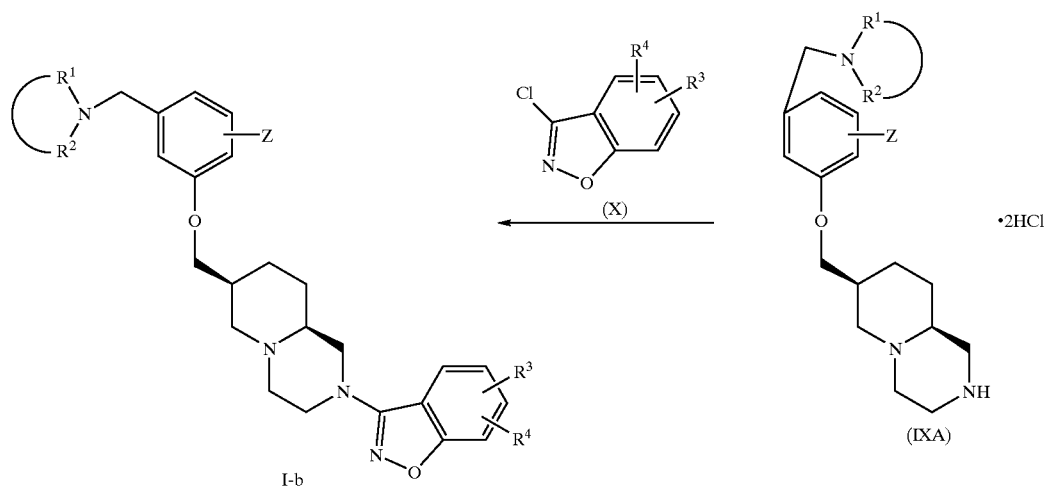

SCHEME 4
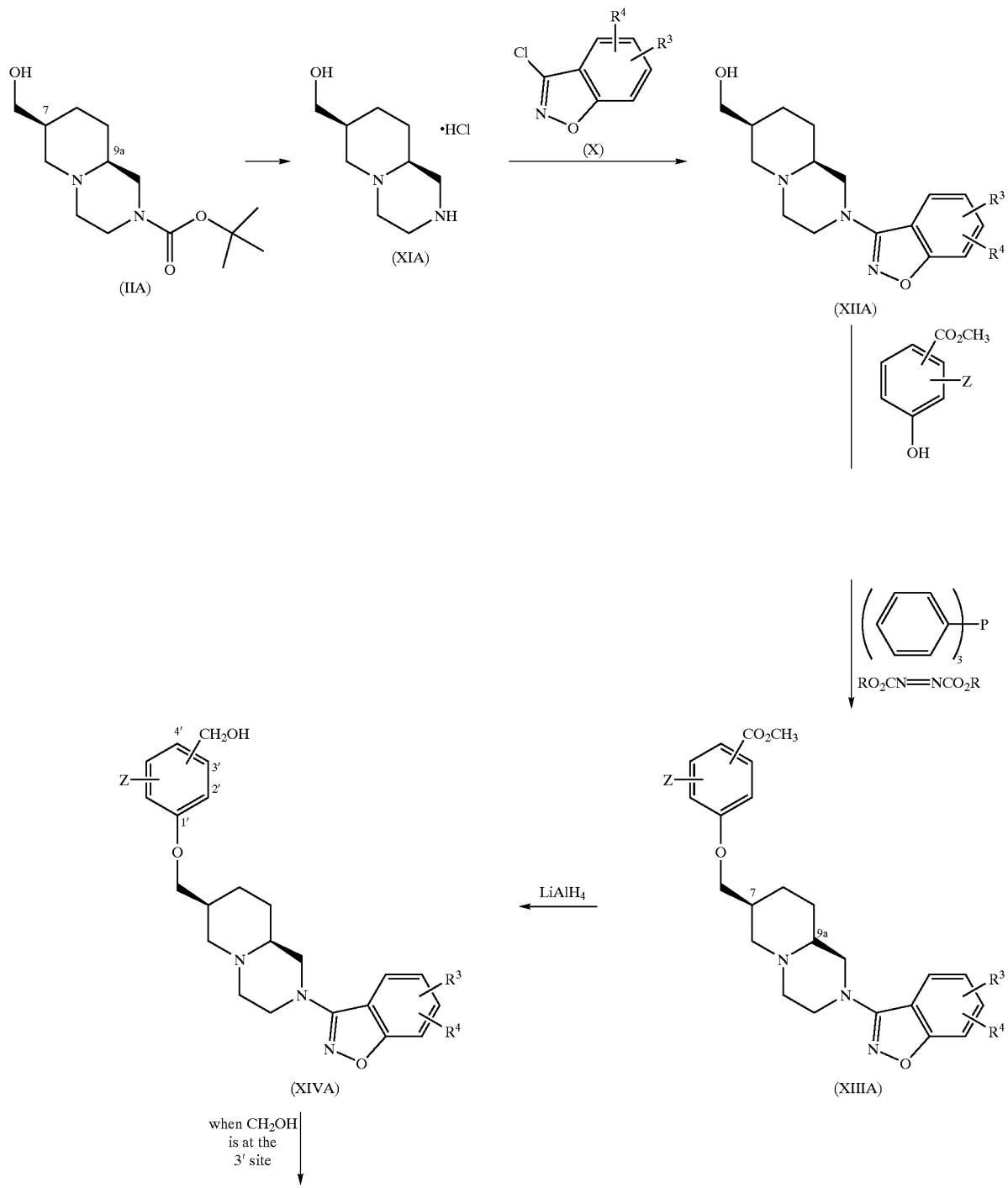

-continued
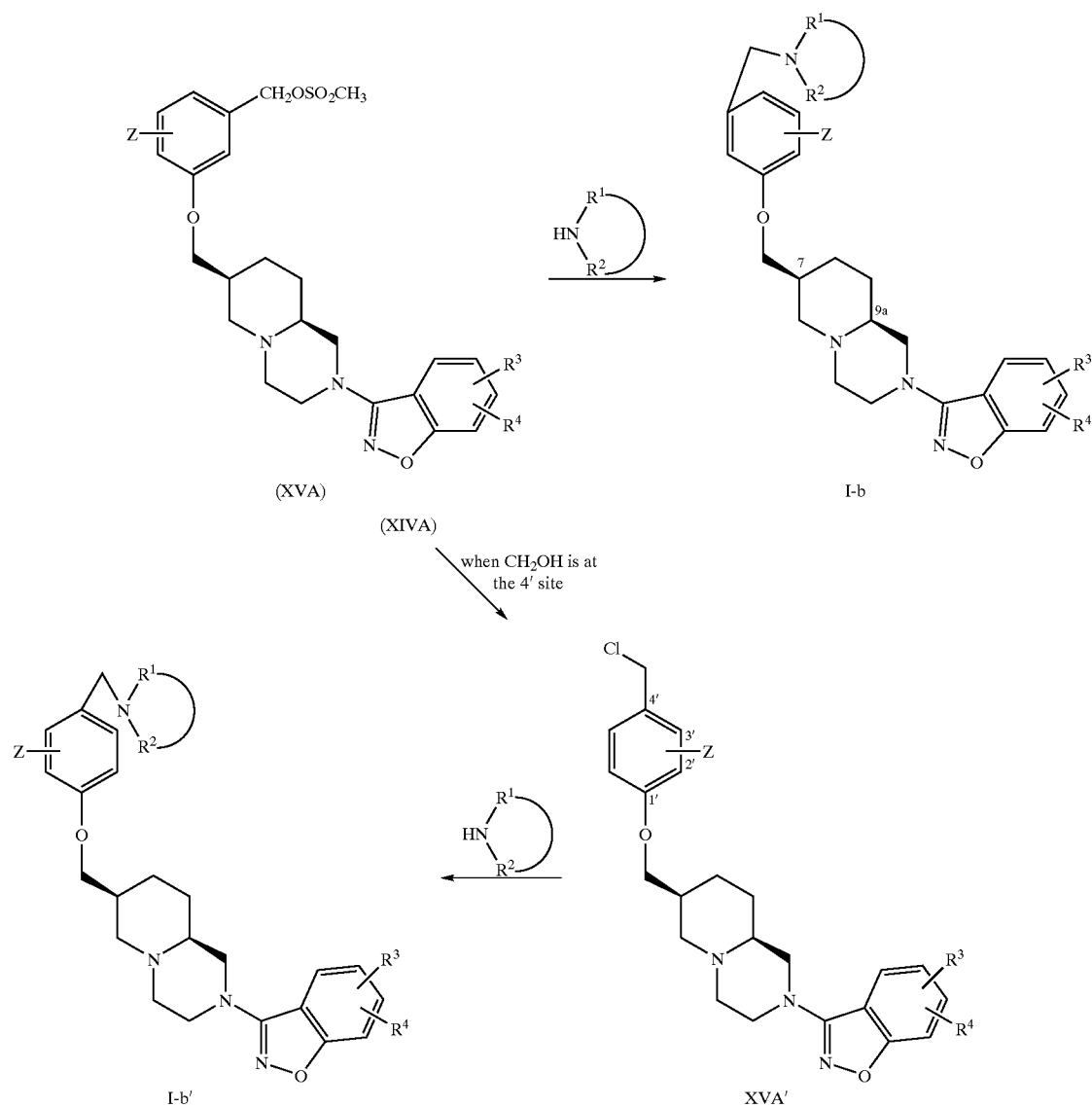
SCHEME 5
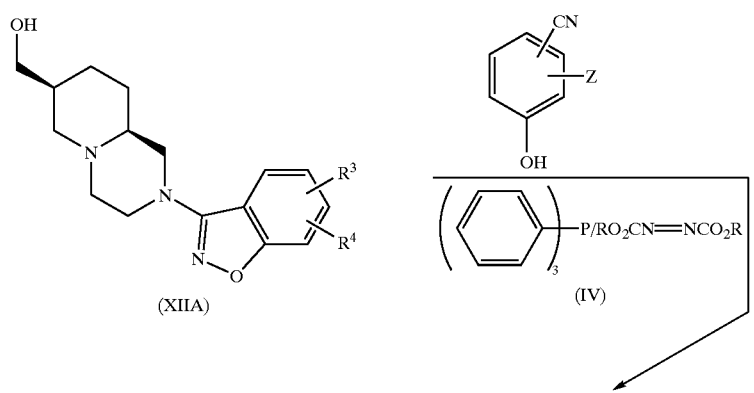

-continued
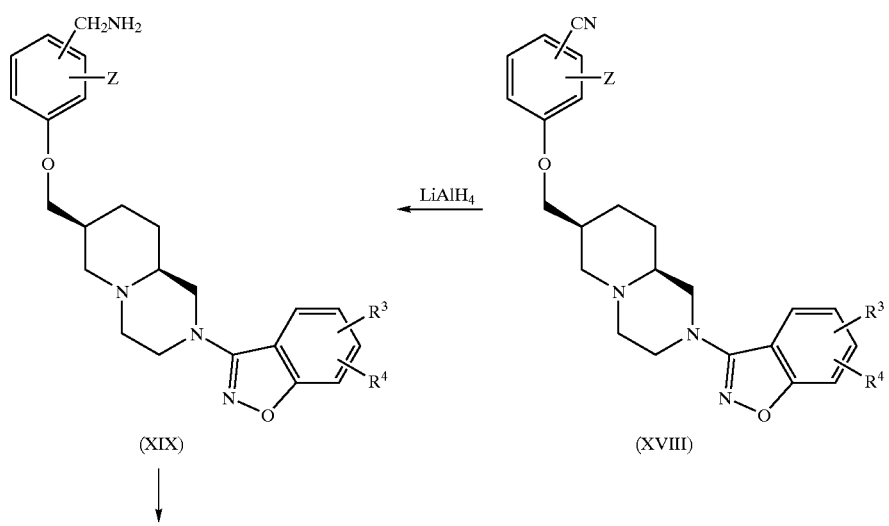
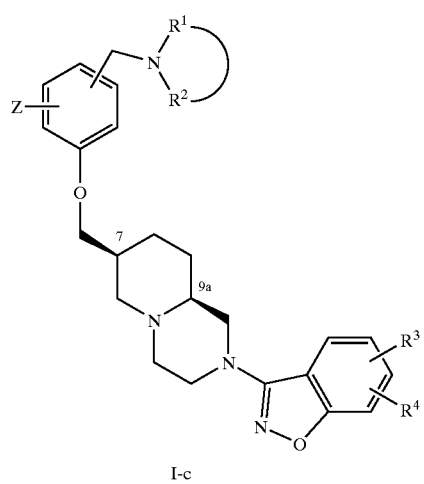
SCHEME 5a
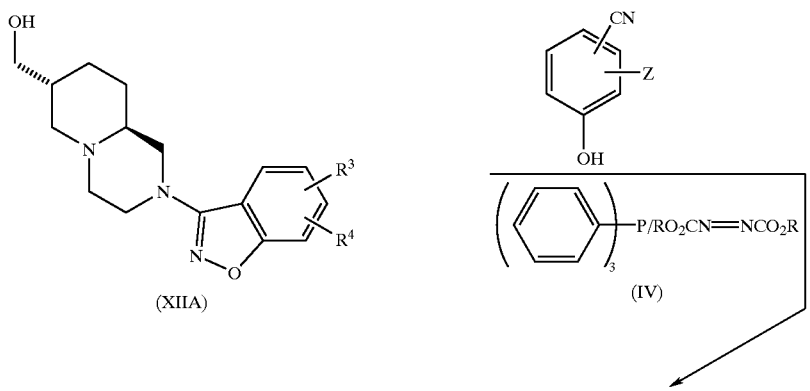

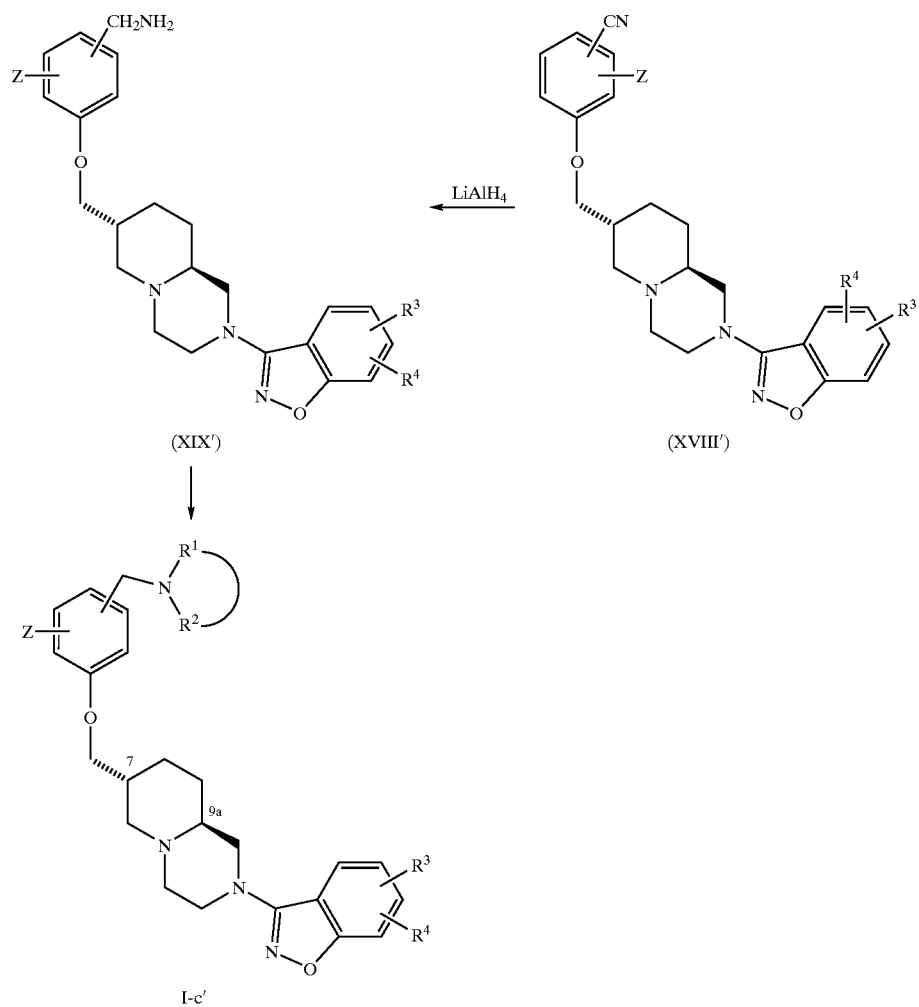
SCHEME 6
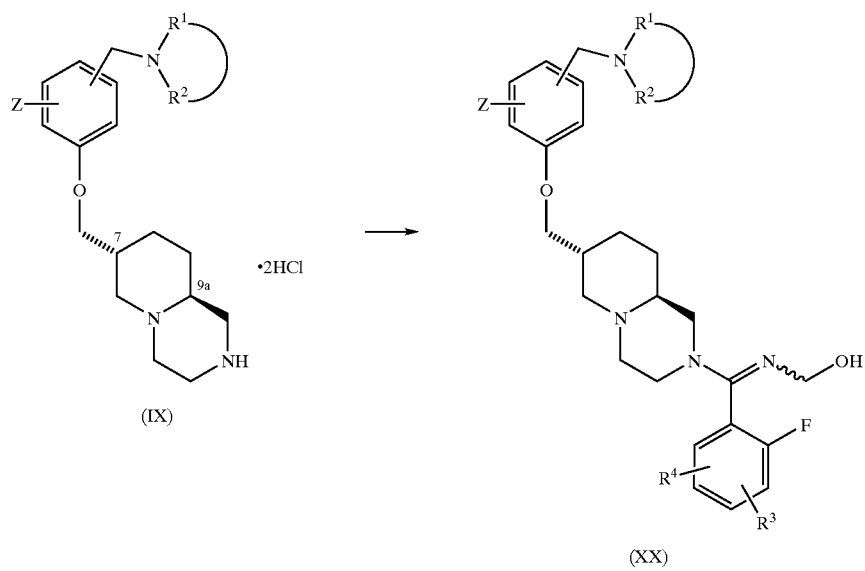

-continued
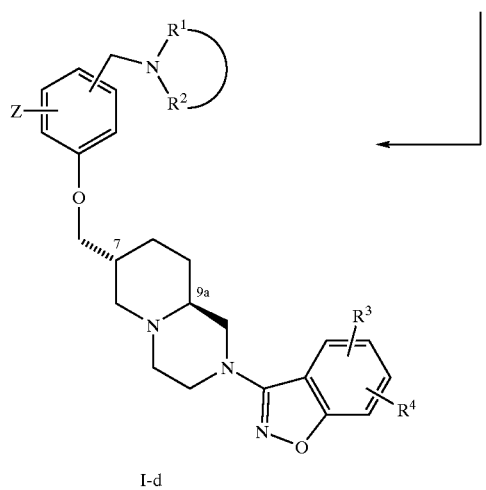
I-d
SCHEME 7
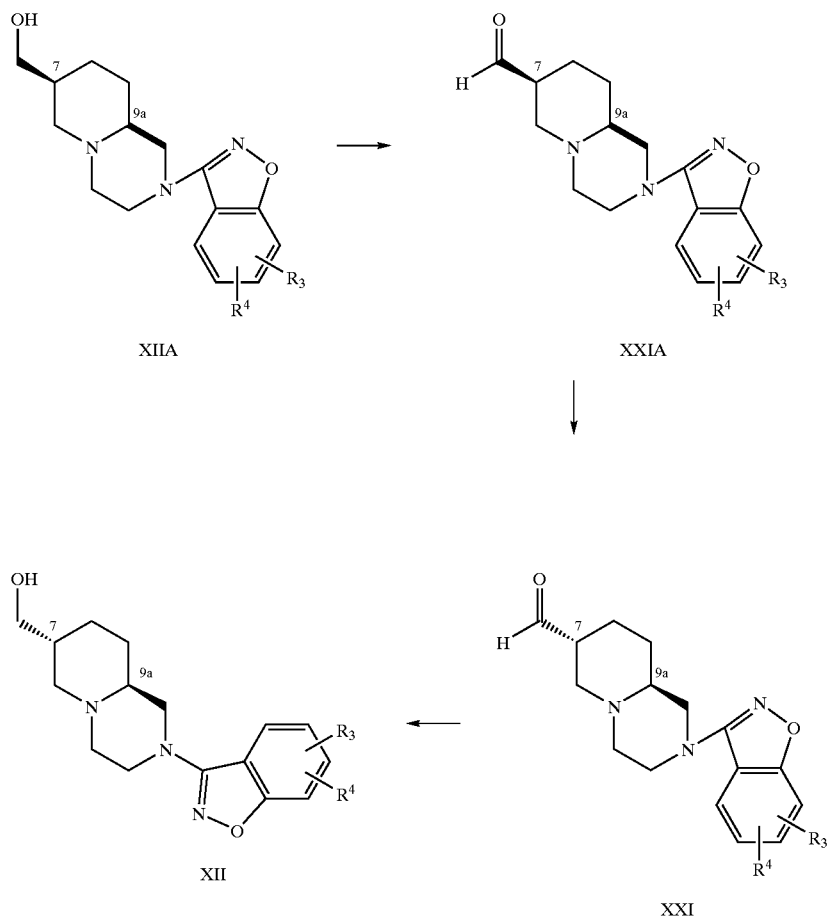

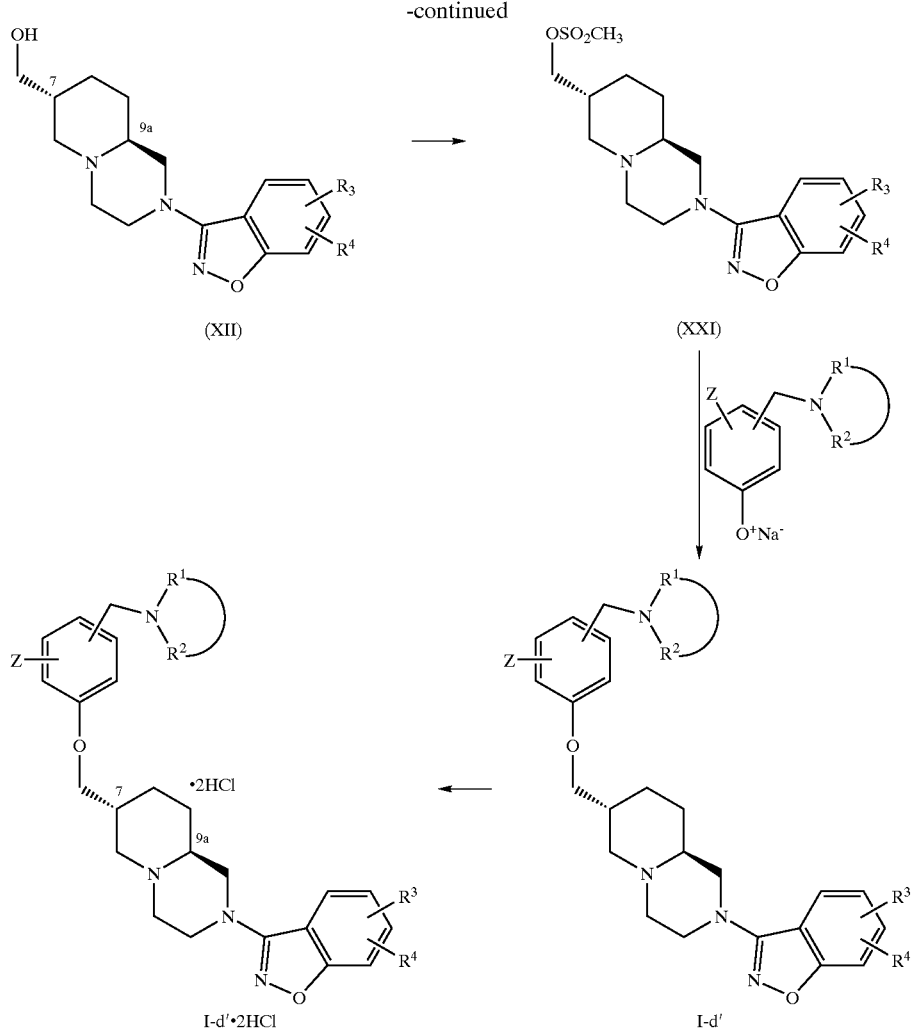

Schemes 1–7 illustrate methods of preparing compounds of the formula I.

Scheme 1 illustrates a method of preparing compounds of the formula I having the (7R, 9aS)-trans stereochemistry. Referring to Scheme 1, the, compound formula II is combined with the compound of formula III, under Mitsunobu coupling conditions, in the presence of triphenylphosphine and a compound of the formula $RO_2CN=NCO_2R$ (IV), wherein R is methyl or ethyl, to form the compound of formula V. (See O. Mitsunobu, *Synthesis*, 1 (1981)). Suitable solvents for this reaction include tetrahydrofuran (THF), other ethers and halocarbon solvents, with THF being preferred. This reaction is generally conducted at a temperature from about room temperature to about 65° C., for about 1 to about 24 hours. It is preferably conducted at about 50° C. for about 4 to 18 hours.

Reduction of the compound of formula V yields the compound of formula VI. This reduction can be accomplished using lithium aluminum hydride as the reducing agent, in a solvent selected from, diethyl ether and other dialkyl ethers, preferably diethyl ether, at a temperature from about −5° C. to about room temperature, for about 0.5 to about 18 hours.

The compound of formula VI can then be converted into the compound of formula VII by reacting it with methanesulfonyl chloride, in the presence of a tertiary amine base such as triethylamine (TEA), in methylene chloride or another halocarbon solvent, at a temperature from about −5° C. to about room temperature, for a period of about 10 minutes to about 2 hours.

Reaction of the resulting compound of formula VII with a compound of the formula $HNR^1R^2$, wherein $R^1$ and $R^2$, together with the nitrogen to which they are attached, may form a ring, as depicted in Scheme 1, yields the corresponding compound having formula VIII. Typically, this reaction is carried out in THF, N,N-dimethylformamide (DMF) or acetonitrile, or a mixture of two or more or the foregoing solvents, at a temperature from about room temperature to about 100° C., for a period from 1 to about 18 hours. The compound of formula VIII is then deprotected to form the hydrochloric acid addition salt of the corresponding compound of formula IX. This can be accomplished using anhydrous hydrochloric acid (HCl) in diethyl ether, another dialkyl ether or a halocarbon solvent at about room temperature. This reaction can also be carried out without a solvent using trifluoroacetic acid, in which case the bitrifluoroacetic acid addition salt is formed. This reaction is generally run from about 2 to about 18 hours.

The desired corresponding compound of formula I-a can be formed by reacting the compound of formula IX from the foregoing reaction with the appropriate compound of formula X, wherein $R^3$ and $R^4$ are as defined above in the definition of compounds of the formula I, and 1,8-diazabicyclo[5.4.0]-undec-7-ene (DBU). This reaction is typically conducted in pyridine, at a temperature from about 50° C. to about 110° C., for a period of about 1 to about 48 hours.

Scheme 2 illustrates an alternate method of making compounds of the formula I-a. Referring to Scheme 2, the starting material of formula II is deprotected using the conditions and reactants described above for the preparation of compounds of the formula IX, to form the dihydrochloric acid or ditrifluoroacetic acid addition salt of the resulting compound of formula XI. Reaction of the resulting compound of formula XI, in the presence of an organic base such as DBU, with the compound of formula XI yields the corresponding compound of formula XII.

The compound of formula XII produced in the foregoing reaction is then reacted with 3-hydroxybenzoic acid methyl ester (III), in the presence of triphenylphosphine and a compound of the formula $RO_2CN\!=\!NCO_2R$ (IV), wherein R is methyl or ethyl, using the reaction conditions described above for the preparation of compounds of the formula V, to form the corresponding compound of formula XII, which is then reduced, to form the corresponding compound of formula XIV. The reduction can be accomplished using lithium aluminum hydride as the reducing agent, in a solvent selected form THF, diethyl ether and other dialkylethers, preferably THF, at a temperature from about −5° C. to about room temperature, for about 0.5 to about 18 hours.

The compound of XIV is then converted into the corresponding compound of formula XV in a manner analogous to the conversion of the compound of formula VI into that of formula VII, which is illustrated in Scheme 1 and described above. The desired final product of formula I-a can then be obtained-from the corresponding compound of the formula XV and the appropriate compound of formula $HNR^1R^2$, wherein $R^1$ and $R^2$, together with the nitrogen to which the are attached, may form a ring, as depicted in Scheme 2, using the procedures described above for converting the compound of formula VII into a compound of the formula VIII.

Scheme 3 Illustrates the preparation of compounds of the formula I having the (7S, 9aS)-cis stereochemistry. These compounds are defined in Scheme 3 and hereinafter as compounds of the formula I-b. The reactions illustrated in this scheme are carried out using reagents and conditions analogous to those described above in Scheme 1 for converting the compound of formula II into a compound of the formula I-a.

Scheme 4 illustrates alternate methods of making compounds of the formula I-b. As illustrated in Scheme 4, compounds of the formula I-b wherein the aminomethyl containing sidechain is attached to the phenoxy group at the 3' position can be made using a procedure analogous to that of Scheme 2. The analogous compounds wherein the aminomethyl sidechain is attached to the phenoxy group at the 4' position proceed through a different intermediate. Specifically, such compounds can be prepared by reacting the corresponding compound of the formula XIVA, wherein the hydroxymethyl group is at the 4' position, with methanesulfonyl chloride, under the same reaction conditions described above for the formation of the compound of formula VII in Scheme 1, to form the corresponding compound having the formula XVA'. This compound can then be converted into the corresponding compound having the formula I-b' using a procedure analogous to that described above for the formation of compounds of the formula I-a from the corresponding compounds of formula XV.

Schemes 5 and 5a illustrate a method for preparing compounds of the formula I wherein W is $CH_2NR^1R^2$. The series of reactions illustrated in Scheme 5 for converting the starting materials of the formula XIIA into those of the formula XIX is analogous to the transformation of the compound of formula XIIA into a compound of the formula XIVA in Scheme 4, with the exception that in the first step of this series, i.e., the reaction that adds the phenoxy substituent, the substituted phenolic reactant is a cyano substituted phenol rather than a hydroxy substituted benzoic acid methyl ester.

The compound of formula XIX can be converted into the desired final product of formula I-c by reacting it with a compound of the formula $X'\!-\!R^1\!-\!R^2\!-\!X'$, wherein X' is bromo, chloro or methanesulfonate and the dashed line represents the portion of the ring structure of the final product connecting $R^1$ and $R^2$, in the presence of a base such as sodium carbonate or an organic base such as DBU, or with compounds of the formulas $R^1X'$ and $R^2X'$, sequentially. The reaction with $X'\!-\!R^1\!-\!R^2\!-\!X'$ (or the sequential reactions with $R^1X'$ and $R^2X'$) is generally carried out in a solvent such as N,N-dimethylformamide (DMF), THF or methylene chloride, at a temperature from about room temperature to about 100° C., preferably from about 40° C. to about 100° C., for a period of about 1 to 48 hours. The reactions depicted in Scheme 5a can be carried out in an analogous fashion to those of Scheme 5.

Scheme 6 refers to an alternate method of preparing compounds of a formula I having the same stereochemistry at positions 7 and 9a as compounds of the formula I-a, and wherein the aminomethyl sidechain on the phenoxy group can be attached at any position (i.e., ortha, meta or para) of that group. These compounds are referred to in Scheme 6 and hereinafter as compounds of the formula I-d. Referring to Scheme 6, the dihydrochloride salt of the appropriate compound of the formula IX is reacted with syn, anti, or a mixture of the syn and anti isomers of a compound of the formula

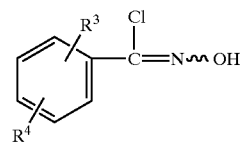

(i.e., the appropriately substituted benzohydroximinoyl chloride), in the presence of a base such as DBU, to form the corresponding compound of formula XX. Suitable solvents for this reaction include chlorohydrocarbons such as chloroform and methylene chloride. Suitable reaction temperatures range from about −78° C. to about 50° C. This reaction is preferably conducted at a temperature from about 20° C. to about 40° C., for a period of about 0.5 to about 24 hours.

The resulting compound of formula XX can then be converted into the desired final product of formula I-d by reacting it with a strong nucleophilic organic base (e.g., n-butyl lithium) or sodium hydride. This reaction is typically conducted in a solvent such as toluene, DMF or THF, at a temperature from about room temperature to about 110° C. for about 1 to 48 hours. Preferably, the solvent is a mixture of toluene and THF and the reaction is carried out at a temperature from about 80° C. to about 100° C.

Scheme 7 illustrates an alternate method that can be used to form compounds of the formula I-a and the analogous compounds wherein the aminomethyl sidechain is attached to the phenoxy group at the ortho, meta or para positions. Such compounds are referred to in Scheme 7 and hereinafter as "compounds of the formula I-d'". Referring to Scheme 7, a compound of the formula XIIA is oxidized to form the corresponding (7S,9aS)-cis aldehyde of formula XXIA by dissolving it in dichloromethane containing an excess of N,N-diisopropylethylamine, (in molar equivalents, with respect to the substrate of formula (XIIA)), and treating it with a slurry of pyridine-sulfur trioxide complex in dimethylsulfoxide (DMSO) at an initial temperature below 10° C. The reaction mixture is then stirred at about ambient temperature for about 18 hours. The resulting compound of formula XXIA is then epimerized at the C-7 carbon to form the corresponding (7R, 9aS)-trans aldehyde of formula XXI by stirring a methanol solution of the compound of formula XXIA it with solid potassium carbonate at about ambient temperature for about 18 hours.

Reduction of the aldehyde of formula XXI yeilds the corresponding alcohol of formula XII. This reduction can be accomplished by treatment with sodium borohydride in methanol for about 18 hours at about ambient temperature.

The compound of formula XII is reacted with methanesulfonyl chloride, in the presence of a base such as DBU, in methylene chloride, at a temperature from about −5° C. to about room temperature, for about 10 minutes to about 2 hours. The resulting compound of formula XXI is then reacted with sodium phenolate, wherein the phenyl moiety is substituted with a group of the formula $CH_2NR^1R^2$ wherein $R^1$ and $R^2$, together with the nitrogen to which they are attached, may form a ring, as described above, to form the desired final product of formula I-d'. Examples of solvents in which this reaction can be conducted are DMF and N-methylpyrrolidinone (NMP). The preferred solvent is NMP. The reaction temperature can range from about 20° C. to about 100° C., and is preferably between about 70° C. and about 100° C. Generally, the reaction is run for a period for about 1 to 24 hours. As illustrated in Scheme 7, the resulting compound of formula I-d' can be converted into the corresponding dihydrochloride salt using methods well known to those of skill in the art. For example, such compound can be treated with 12N hydrochloric acid in acetone, or with anhydrous hydrochloric acid in a mixture of diethyl ether and ethyl acetate or dichloromethane.

All of the above schemes and corresponding discussions with the exception of Schemes 5 and 5a, the moieties represented as —$CH_2NR^1R^2$ and

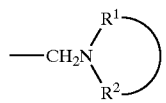

are interchangeable. Also, the same reactions apply to the formation of compounds of the formula I wherein W is alkoxy rather than —$CH_2NR^1R^2$, in which case the reactant —$NHR^1R^2$ is replaced by $M^+O^-$—$(C_1-C_6)$alkyl, wherein $M^+$ is a suitable monovalent cation such as a sodium or lithium cation.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Compounds of the formula I and their pharmaceutically acceptable salts (hereinafter also referred to, collectively, as "the active compounds") are useful psychotherapeutics and are potent agonists and/or antagonists of the senotonin 1A (5-HT1A) and/or serotonin 1D (5-HT1D) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania and headache (associated with vascular disorders).

The affinities of the compounds of this invention for the various serotonin-1 receptors can be determined using standard radioligand binding assays as described in the literature. The 5-HT1A affinity can be measured using the procedure of Hoyer et al. (*Brain Res.*, 376, 85 (1986)). The 5-HT1D affinity can be measured using the procedure of Heuring and Peroutka (*J. Neurosci.*, 7, 894 (1987)).

The in vitro activity of the compounds of the present invention at the 5-HT1 D binding site may be determined according to the following procedure. Bovine caudate tissue is homogenized and suspended in 20 volumes of a buffer containing 50 mM TRIS-hydrochloride (tris [hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS-hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS-hydrochloride containing 0.01 percent ascorbic acid with a final pH of 7.7 and also containing 10 mM pargyline and 4 mM calcium chloride ($CaCl_2$). The suspension is kept on ice at least 30 minutes prior to use.

The inhibitor, control or vehicle is then incubated according to the following procedure. To 50 ml of a 20 percent dimethylsulfoxide (DMSO)/80 percent distilled water solution is added 200 ml of tritiated 5-hydroxytryptamine (2 nM) in a buffer of 50 mM TRIS-hydrochloride containing 0.01 percent ascorbic acid at pH 7.7 and also containing 10 mM pargyline and 4 mM calcium chloride, plus 100 nM of 8-hydroxy-DPAT (dipropylaminotetraline) and 100 nM of mesulergine. To this mixture is added 750 ml of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters). The pellet is then washed three times with 4 ml of a buffer of 50 mM TRIS-hydrochloride at pH 7.7. The pellet is then placed in a scintillation vial with 5 ml of scintillation fluid (aquasol 2) and allowed to sit overnight. The percent inhibition can be calculated for each dose of the compound. An $IC_{50}$ value can then be calculated from the percent inhibition values.

The activity of the compounds of the present invention for 5-HT1A binding ability can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supernate separated and recentrifuged at 70,000 G for 15 minutes. The supernate is discarded and the pellet re-suspended in 10 volumes of 15 mM TRIS-hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS-hydrochloride at pH 7.7 containing 4 mM of calcium chloride and 0.01 percent ascorbic acid. The tissue is stored at -70° C. until ready for an experiment. The tissue can be thawed immediately prior to use, diluted with 10 mm pargyline and kept on ice.

The tissue is then incubated according to the following procedure. Fifty microliters of control, inhibitor, or vehicle (1 percent DMSO final concentration) is prepared at various dosages. To this solution is added 200 ml of tritiated DPAT at a concentration of 1.5 nM in a buffer of 50 mM TRIS-hydrochloride at pH 7.7 containing 4 mM calcium chloride, 0.01 percent ascorbic acid and pargyline. To this solution is then added 750 ml of tissue and the resulting suspension is vortexed to ensure homogeneity. The suspension is then incubated in a shaking water bath for 30 minutes at 37° C. The solution is then filtered, washed twice with 4 ml of 10 mM TRIS-hydrochloride at pH 7.5 containing 154 mM of sodium chloride. The percent inhibition is calculated for each dose of the compound, control or vehicle. $IC_{50}$ values are calculated from the percent inhibition values.

The compounds of formula I of the present invention described in the following Examples were assayed for 5-HT1A and 5-HT1D affinity using the aforementioned procedures. All such compounds of the invention that were tested exhibited $IC_{50}$'s less than 0.60 mM for 5-HT1D affinity and $IC_{50}$'s less than 1.0 mM for 5-HTIA affinity.

The agonist and antagonist activities of the compounds of the invention at 5-HT1A and 5-HT1D receptors can be determined using a single saturating concentration according to the following procedure. Male Hartley guinea pigs are decapitated and 5-HT1A receptors are dissected out of the hippocampus, while 5-HT1D receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 mM GTP and 0.5–1 microcuries of [32P]-ATP (30 Ci/mmol: NEG-003—New England Nuclear). Incubation is initiated by the addition of tissue to siliconized microfuge tubes (in triplicate) at 30° C. for 15 minutes. Each tube receives 20 mL tissue, 10 mL drug or buffer (at 10× final concentration), 10 mL 32 nM agonist or buffer (at 10× final concentration), 20 mL forskolin (3 mM final concentration) and 40 mL of the preceding reaction mix. Incubation is terminated by the addition of 100 mL 2% SDS, 1.3 mM CAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 mM (R)-8-OH-DPAT for 5-HT1A receptors, and 320 nM 5-HT for 5-HT1D receptors. Percent inhibitions by the test compounds are then calculated in relation to the inhibitory effect of (R)-8-OH-DPAT for 5-HT1A receptors or 5-HT for 5-HT1D receptors. The reversal of agonist induced inhibition of forskolin-stimulated adenylate cyclase activity is calculated in relation to the 32 nM agonist effect.

The compounds of the invention can be tested for in vivo activity for antagonism of 5-HT1D agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-HT1D agonist, such as [3-(1-methylpyrrolidin-2-ylmethylyl)-1H-indol-5-yl]-(3-nitropyridin-3-yl)-amine, which can be prepared as described in PCT publication WO93/111 06, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT1D agonist is then administered at 0 minutes and temperatures are taken 30, 60, 120 and 240 minutes later.

In subcutaneous screening experiments, a pre-drug baseline temperature reading is made at −30 minutes. The test compound and 5-HT1D agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin 5-HT1 agonist activity can be determined by the in vitro receptor binding assays, as described for the 5-HT1A receptor using rat cortex as the receptor source and [$^3$H]-8-OH-DPAT as the radioligand [D. Hoyer et al. *Eur. J. Pharm.*, 118, 13 (1985)] and as described for the 5-HT1D receptor using bovine caudate as the receptor source and [3H]serotonin as the radioligand [R. E. Heuring and S. J. Peroutka, *J. Neuroscience*, 7, 894 (1987)]. Of the active compounds tested, all exhibited an $IC_{50}$ in either assay of 1 mM or less.

The compounds of formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g. isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g, benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5-HT re-uptake inhibitor is referred herein to as "the active combination"), are useful psychotherapeutics and may be used in the treatment or prevention of disorders the treatment or prevention of which is facilitated by modulating serotonergic neurotransmission such as hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas. e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 mg to 1000 mg of the compound of the invention. The overall daily dose with an aerosol will be within the range 100 mg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 47–61 mesh silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

(7S, 9aS)-CIS-1-[3-(2-BENZO[d]ISOXAZOL-3-YL-OCTAHYDRO-PYRIDO[1,2-a]PYRAZIN-7-YLMETHOXY)-BENZYL]-AZETIDIN-3-OL (DIASTEREOMERS)

Step 1

(7S,9aS)-cis-7-(3-methoxycarbonyl-phenoxymethyl)-octahydro-pyrido[1,2-a]pyrazine-2-carboxylic acid tert-butyl ester Utilizing (7R,9aS)-cis-7-(hydroxymethyl)-2-(tert-butoxycarbonyl)-2,3,4,6,7,8,9,9a-octahydro-1H-pyrido[1,2-a]pyrazine (European Patent Application EP 646116, published Apr. 5, 1995; 8.14 g., 30 mmol) in place of the corresponding (7R,9aS)-trans isomer as a reactant in the procedure of Example 5, Step 1 (with appropriate scaling of other reactants/solvents), the title compound was prepared as a colorless oil (8.80 g, 73% yield; flash chromatography: silica gel, 47–61 micron mesh; elution with ethyl acetate/hexane=2:8 in volume). MS m/z 405 (M+1).

Step 2

(7S, 9aS)-cis-7-(3-hydroxymethyl-phenoxyacetyl)-octahydro-pyrido[1,2-a]pyrazine-2-carboxylic acid tert-butyl ester Utilizing the general procedure described in Example 5, Step 2 and substituting the product of the previous step for the corresponding (7R,9aS)-trans isomer as a reactant (8.80 g, 21.8 mmol) and appropriate scaling of other reactants/solvents, the title compound was prepared (7.39 g, 90% yield) as a colorless oil. MS m/z 377 (M+1).

Step 3

(7S, 9aS)-cis-7-[3-(3-Hydroxy-azetidin-1-ylmethyl)-phenoxymethyl]-octahydro-pyrido[1,2-a]pyrazine-2-carboxylic acid tert-butyl ester (diastereomers)

Utilizing the general procedure Example 5, Step 3, and substituting as reactants the title compound of the previous step (307 mg, 0.82 mmol) for the corresponding (7R,9aS)-trans isomer and (R,S)-3-hydroxy-azetidine (175 mg, 2.4 mmol), with appropriate scaling of other reagents/solvents, the title compound was prepared as a colorless oil (224 mg, 63% yield; flash chromatography: silica gel, 47–61 micron mesh; elution with methanol/methylene chloride=8:92 in volume). $^{13}$C NMR (75 MHz, CDCl$_3$) δ159.6, 154.8, 139.0, 129.3 120.7, 114.6, 113.7, 79.6, 68.7, 64.1, 63.5, 62.8, 61.0, 56.5, 54.8, 33.7, 28.4, 25.0, 24.7 ppm. MS m/z 432 (M+1).

Step 4

(7S, 9aS)-cis-1-[3-(Octahydro-pyrido[1,2-a]pyrazin-7-ylmethoxy)-benzyl]-azetidin-3-ol (diastereomers)

Utilizing the general procedure of Example 5, Step 4, and substituting as a reactant the title compound of the previous step (224 mg, 0.52 mmol) for the corresponding (7R,9aS)-trans isomer, with appropriate scaling of other reactants/solvents the title compound was prepared (dihydrochloride salt) as a colorless viscous oil (100 mg, 48% yield).

Step 5

(7S, 9aS)-cis-1-[3-(2-Benzo[d]isoxazol-3-yl-octahydro-pyrido[1,2-a]pyrazin-7-ylmethoxy)-benzyl]-azetidin-3-ol (diastereomers)

Utilizing the general procedure of Example 5, Step 5, and substituting the title compound from the previous step (100 mg, 0.25 mmol) for the corresponding (7R,9aS)-trans isomer as a reactant, with proper scaling of other reactants/solvents, the title compound was prepared in free base form (39 mg, 35% yield) as a colorless oil (flash chromatography: silica gel, 47–61 micron mesh; elution with methanol/methylene chloride=8:92 in volume). $^{13}$C NMR (75 MHz, CDCl$_3$) δ164.0, 161.2, 159.4, 139.4, 129.5, 129.4, 122.2, 120.7, 116.3, 114.6, 113.6, 110.5, 68.7, 64.1, 63.6, 62.7, 60.4, 56.5, 54.2, 53.7, 48.3, 33.7, 25.1, 24.8 ppm. MS m/z 449 (M+1). The dihydrochloride was readily prepared from the free base in amorphous form using the general procedure of Example 5, Step 5.

EXAMPLE 2

(7R,9aS)-CIS[3-(2-BENZO[d]ISOXAZOL-3-YL-OCTAHYDRO-PYRIDO[1,2-a]PYRAZIN-7-YLMETHOXY)-BENZYL]-CYCLOPROPYL-AMINE

Step 1

(7S,9aS)-cis-7-(3-Cyproylaminomethyl-phenoxymethyl)-octahydro-pyrido[1,2-a]pyrazine-2-carboxylic acid tert-butyl ester Utilizing the title compound of Example 1/Step 2 (750 mg, 2.0 mmol) and cyclopropylamine (414 μL, 6.0 mmol) as reactants; and the general procedure of Example 1/Step 3, with appropriate scaling of other reagents/solvents, the title compound was prepared as a colorless oil (431 mg, 52% yield; flash chromatography: silica gel, 47–61 micron mesh; elution with methanol/methylene chloride=4:96 in volume). MS m/z 416 (M+1).

Step 2

(7S,9aS)-cis-Cyclopropyl-[3-(octahydro-pyrido[1,2-a]pyrazin-7-ylmethoxy)-benzyl]-amine dihydrochloride Utilizing the title compound from the previous step (431 mg, 1.0 mmol) and the appropriately scaled reactant/ solvents and general procedure of Example 1/Step 4, the title compound was prepared and isolated (dihydrochloride salt) as a colorless amorphous solid (357 mg, 88% yield).

MS m/z 316 (M+1).

Step 3

(7S,9aS)-cis-[3-(2-Benzo[d]isoxazol-3-yl-octahydro-pyrido[1,2-a]pyrazin-7-ylmethoxy)-benzyl]-cyclopropyl-amine Utilizing the title compound from the previous step (200 mg, 0.52 mmol), 3-chloro-benzo[d]isoxazole (98 mg, 0.64 mmol), and 1,8-diazabicyclo[5.4.0]-undec-7-ene (256 μl, 1.69 mmol) as reactants, pyridine (250 μl) as solvent, and the general procedure of Example 1 (with proper scaling of reactants/solvents), the title compound was prepared in free base form (60 mg, 27% yield) as a colorless oil (flash chromatography: silica, 47–61 micron mesh; elution with methanol/methylene chloride=4:96 in volume). The title compound product was identical in all respects to the title compound product of Example 19.

EXAMPLE 3

(7S,9aS)-CIS-2-BENZO[d]ISOXAZOL-3-YL-7-[3-(2-METHOXYMETHYL-PYRROLIDIN-1-YLMETHYL)-PHENOXYMETHYL]-OCTAHYDRO-PYRIDO[1,2-a]PYRAZINE

Step 1

(7S,9aS)-cis-7-[3-(2-Methoxymethyl-pyrrolidin-1-ylmethyl)-phenoxymethyl]-octahydro-pyrido[1,2-a]pyrazine-2-carboxylic acid tert-butyl ester Utilizing the title compound of Example 1/Step 2 (750 mg, 2 mmol) and 2S-methoxymethylpyrrolidine (Aldrich Chemical Co.; 740 μl, 6 mmol) as reactants; and the general procedure of Example 1/Step 3, with appropriate scaling of other reagents/solvents, the title compound was prepared as a colorless oil (449 mg, 47% yield; flash chromatography: silica gel, 47–61 micron mesh; elution with methanol/methylene chloride=6:94 in volume).

MS m/z 474 (M+1);

$^{13}$C NMR (100 MHz, CDCl$_3$) δ159.1, 154.5, 141.2, 128.9, 121.1, 115.2, 112.7, 79.4, 76.4, 68.5, 62.9. 60.9, 59.6, 59.0, 56.4, 54.7, 54.6, 33.6, 28.4, 28.3, 24.9, 24.6, 22.7

Step 2

(7S,9aS)-cis-7-[3-(2-Methoxymethyl-pyrrolidin-1-ylmethyl)-phenoxymethyl]-octahydro-pyrido[1,2-a]pyrazine dihydrochloride Utilizing the title compound from the previous step (449 mg, 0.95 mmol) and the appropriately scaled reactant/solvents and general procedure of Example 1/Step 4, the title compound was prepared and isolated (dihydrochloride salt) as a colorless amorphous solid (428 mg, quantitative yield).

MS m/z 373 (M+1).

Step 3

(7S,9aS)-cis-Benzo[d]isoxazol-3-yl-7-[3-(2-methoxymethylpyrrolidin-1-ylmethyl)-phenoxymethyl]-octahydro-pyrido[1,2-a]pyrazine Utilizing the title compound from the previous step (250 mg, 0.56 mmol), 3-chloro-benzo[d]isoxazole (106 mg, 0.69 mmol), and 1,8-diazabicyclo[5.4.0]-undec-7-ene (273 μl, 1.8 mmol) as reactants, pyridine (260 μl) as solvent, and the general procedure of Example 1 (with proper scaling of reactants/solvents), the title compound was prepared in free base form (107 mg, 37% yield) as a colorless oil (flash chromatography: silica, 47–61 micron mesh; elution with methanol/methylene chloride=5:95 in volume). The title compound product was identical in all respects to the title compound product of Example 18.

EXAMPLE 4

(7S,9aS)-CIS-2-BENZO[d]ISOXAZOL-3-YL-7-[3-(4-ETHYL-PIPERAZIN-1-YLMETHYL-PHENOXYMETHYL]-OCTAHYDRO-PYRIDO[1,2-a]PYRAZINE

Step 1

(7S,9aS)-cis-7-[3-(4-Ethyl-piperazin-1-ylmethyl)-phenoxymethyl]-octahydro-pyrido[1,2-a]pyrazine-2-carboxylic acid tert-butyl ester Utilizing the the compound of Example 1/Step 2 (750 mg, 2.0 mmol) and N-ethyl piperazine (762 μl, 6.0 mmol) as reactants; and the general procedure of Example 1/Step 3, with appropriate scaling of other reagents/solvents, the title compound was prepared as a colorless oil (430 mg, 46% yield; flash chromatography: silica gel, 47–61 micron mesh; elution with methanol/methylene chloride=8:92 in volume).

MS m/z 473 (M+1);

$^{13}$C NMR (100 MHz, CDCl$_3$) δ163.0, 136.3, 133.9, 126.1, 120.3, 119.4, 82.0. 70.9. 69.4, 63.6, 58.0, 55.5, 54.1, 48.3, 44.1, 37.3, 36.0, 33.7, 26.0, 25.6, 18.0, 6.8.

Step 2

(7S,9aS)-cis-7-[3-(4-Ethyl-piperazin-1-ylmethyl)-phenoxymethyl]-octahydro-pyridol[1,2-a]pyrazine dihydrochloride Utilizing the title compound from the previous step (410 mg, 0.87 mmol) and the appropriately scaled reactant/solvents and general procedure of Example 1/step 4, the title compound was prepared and isolated (dihydrochloride salt) as a colorless amorphous solid (quantitative yield).

MS m/z 373 (M+1).

Step 3

(7S,9aS)-cis-Benzo[d]isoxazol-3-yl-7-[3-(4-ethyl-piperazin-1-ylmethyl)-phenoxymethyl]-octahydro-pyrido[1,2-a]pyrazine Utilizing the title compound from the previous step (250 mg, 0.56 mmol), 3-chloro-benzo[d]isoxazole (106 mg, 0.69 mmol), and 1,8-diazabicyclo[5.4.0]-undec-7-ene (275 μl, 1.8 mmol) as reactants, pyridine (260 μl) as solvent, and the general procedure of Example 1 (with proper scaling of reactants/solvents), the title compound was prepared in free base form (184 mg, 67% yield) as a colorless oil (flash chromatography: silica, 47–61 micron mesh; elution with methanol/methylene chloride=5:95 in volume). The title compound product was identical in all respects to the title compound product of Example 21.

EXAMPLE 5

(7R,9aS)-TRANS-2-(5-FLUORO-BENZO[d]ISOXAZOL-3-YL)-7-(3-PYRROLIDIN-1-YLMETHYL-PHENOXYMETHYL)-OCTAHYDROPYRIDO[1,2-a]PYRAZINE

Step 1

(7R,9aS)-trans-7-(3-methoxycarbonylphenoxymethyl)-octahydro-pyrido-1,2-a]pyrazine-2-carboxylic acid tert-butyl ester To a solution of (7R,9aS)-trans-7-(hydroxymethyl)-2-(tert-butoxycarbonyl)-2,3,4,6,7,8,9,9a-octahydro-1H-pyrido[1,2-a]pyrazine (European Patent Application EP 648,116, published Apr. 5, 1995; 8.5 g, 31 mmol in anhydrous tetrahydrofuran (120 ml), methyl 3-hydroxybenzoic acid (7.18 g, 47 mmol), triphenylphosphine (9.9 g, 38 mmol), and diethylazodicarboxylate (5.94 ml, 38 mmol) were sequentially added. The stirred reaction mixture was heated at 55° C. for 18 hours. The solvent was removed in vacuo, and the residue was extracted with a 10% dilute aqueous sodium bicarbonate/methylene chloride mixture (400 ml of each). The aqueous phase was extracted with three 100 ml portions of fresh methylene chloride. The combined organic extracts were in turn, extracted with 200 ml of 1N aqueous sodium hydroxide and 200 ml of 10% aqueous sodium bicarbonate, and then dried with anhydrous sodium sulfate. Solvent removal in vacuo afforded an oil (30 g). The crude product was purified by flash chromatography (silica gel, 47–61 micro mesh; elution with ethyl acetate/hexane=6:4 in volume) which afforded the title compound (9.36 g, 75% yield) as an amorphous solid.

$^{13}$C NMR (75 MHz, CDCl$_3$) δ166.9, 158.9, 154.6, 131.4, 129.4, 122.0, 119.9, 114.6, 79.7, 71.1, 62.2, 60.8, 58.7, 54.8, 52.1, 36.3, 28.7, 28.4, 26.9, 14.4 ppm;

MS m/z 405 (M+1).

Step 2

(7R,9aS)-trans-7-(3-hydroxymethylphenoxymethyl)-octahydro-pyrido-[1,2-a]pyrazine-2-carboxylic acid tert-butyl ester To an ice bath-chilled solution of the Step 1 title compound (9.36 g, 23 mmol) in anhydrous ether (75 ml), a 1.0M solution of lithium aluminum hydride in diethyl ether (27.6 ml, 27.6 mmol) was added dropwise. The reaction was then stirred for 40 minutes at ambient temperature prior to quenching by cautious dropwise addition of a total of 3 ml of 2N aqueous sodium hydroxide. Tetrahydrofuran (100 ml) was added, and the reaction was stirred for 20 minutes prior to drying by addition of anhydrous sodium sulfate. Filtration through a celite pad and solvent removal in vacuo afforded the title compound as a colorless oil (quantitative yield).

$^{13}$C NMR (100 MHz; CDCl$_3$) δ159.1, 142.9. 129.5, 119.1, 113.5, 112.9, 79.7. 70.8, 67.9, 64.9, 82.1, 60.8, 58.6, 54.7, 36.2, 28.6, 28.4, 26.9, 25.6, 14.4 ppm;

MS m/z 377 (M+1).

Step 3

(7R,9aS)-trans-7-(3-pyrrolidin-1-ylmethylphenoxymethyl)-octahydro-pyrido[1,2-a]pyrazine-2-carboxylic acid tert-butyl ester To an ice bath chilled solution of the title compound from the previous step (5.6 g, 14.9 mmol) and triethylamine (2.60 ml, 18.6 mmol) in anhydrous methylene chloride (95 ml), methanesulfonyl chloride (1.27 ml, 16.3 mmol) was added as a single portion. After 20 minutes of stirring at ca. 5° C., thin layer chromatography inspection (silica gel plates; methanol/methylene chloride=6:94 in volume; aqueous potassium permanganate spray with heat) revealed complete conversion of starting material to the corresponding mesylate [(7R,9aS)-trans-7-(3-methanesulfonyloxymethyl-phenoxymethyl)-octahydro-pyrido[1,2-a]pyrazine-2-carboxylic acid tert-butyl ester]. 10% Aqueous sodium bicarbonate and methylene chloride (100 ml of each) were added, and the mixture was vigorously stirred prior to phase separation. The aqueous phase was then extracted with three 50 ml portion of fresh methylene chloride. The combined organic extracts were dried (anhydrous sodium sulfate), and the solvent was removed in vacuo to isolate the mesylate an oil. The entire sample was dissolved in acetonitrile (95 ml). Pyrrolidine (3.88 ml, 44.7 mmol) was added, and the reaction mixture was then heated at 50° C. for 18 hours. The solvent was removed in vacuo, and the resulting residue was extracted into a 10% aqueous sodium bicarbonate/methylene chloride (200 ml of each) mixture. The aqueous phase was re-extracted with three 50 ml portions of fresh methylene chloride. The combined organic extracts were dried (anhydrous sodium sulfate) and concentrated in vacuo to yield an amber oil (6.75 g). Flash chromatography of the entire sample (silica gel 47–61 micron mesh; elution initially with methanol/methylene chloride=8:92 in volume, increasing methanol content to a final 2:8 volume ratio) afforded the title compound (3.60 g, 56% yield) as a colorless oil.

$^{13}$C NMR (75 MHz, CDCl$_3$) δ159.1, 154.6, 129.2, 121.4, 115.0, 113.4, 79.7, 70.9, 60.8, 60.5, 58.8, 54.8, 54.1, 50.7, 36.4, 28.8, 28.4, 26.9, 23.4 ppm.

Step 4

(7R,9aS)-trans-3-(3-pyrrolidin-1-ylmethyl-phenoxymethyl)-octahydro-quinazolizine dihydrochloride The Step 3 title compound (3.60 g) was dissolved in chloroform (50 ml). Diethyl ether (60 ml) saturated with anhydrous hydrogen chloride gas was added. The reaction mixture was then stirred at 18 hours at ambient temperature. Evaporation of solvent and excess hydrogen chloride afforded the title compound as a dihydrochloride salt (quantitative yield).

Step 5

(7R,9aS)-trans-2-(5-fluoro-benzo[d]isoxazol-3-yl)-7-(3-pyrrolidin-1-ylmethyl-phenoxymethyl)-octahydro-pyrido[1,2-a]pyrazine The Step 4 title compound (dihydrochloride salt; 125 mg, 0.31 mmol), 1,8-diazabicyclo[5.4.0]-undec-7-ene (153 μl, 1.0 mmol), and 3-chloro-5-fluoro-benzo[d]isoxazole (66 mg, 0.39 mmol) were dissolved in pyridine (150 μl). The reaction was heated at 90° C. for 18 hours. 10% aqueous sodium bicarbonate and methylene chloride (15 ml of each) were added to the well-stirred mixture. The aqueous phase was then re-extracted with three 15 ml portions of fresh methylene chloride. The combined organic extracts were dried (anhydrous sodium sulfate) and the solvent was removed in vacuo. Purification of the oily semi-solid residue (150 mg) by flash chromatography (silica gel, 47–61 micron mesh; elution with methanol/methylene chloride=7.5:92.5 in volume) afforded the tile compound (free base) as a colorless amorphous solid (57 mg. 36% yield). Dissolution of the entire sample in ethyl acetate/methylene chloride (1.0 ml of each), addition of a saturated diethyl ether solution of anhydrous hydrogen chloride (3 ml); and finally, solvent removal in vacuo afforded the title compound dihydrochloride as an amorphous solid.

Free base data: $^{13}$C NMR (75 MHz, CDCl$_3$) δ161.62, 160.91, 159.45, 158.45, 141.54, 129.55, 121.70, 118.44, 116.88, 115.28, 113.35, 111.73, 107.76, 71.26, 61.21, 60.55, 59.20, 54.68, 54.60, 54.12, 48.71, 36.88, 29.43, 27.37, 23.90 ppm;

MS m/z 465 (M+1).

EXAMPLE 6

(7R,9aS)-TRANS-1-{3-[2-(5-FLUORO-BENZO[d] ISOXAZOL-3-YL)-OCTAHYDROPYRIDO[1,2-a] PYRAZIN-7-YLMETHOXY]-BENZYL}-AZETIDIN-3-OL (MIXTURE OF DIASTEREOMERS)

Step 1

(7R,9aS)-trans-7-[3-(3-hydroxy-azetidin-1-ylmethyl)-phenoxymethyl]-octahydro-pyrido[1,2-a]pyrazine-2-carboxylic acid tert-butyl ester)

Utilizing the general procedure of Example 5, Step 3, and starting with 2.25 g (6 mmol) of the aforedescribed Example 5/Step 2 title compound and substituting as a reactant (R,S)-3-hydroxyazetidine for pyrrolidine, the title compound was isolated (free base) as a colorless oil (1.48 g, 57% yield; flash chromatography purification: silica gel, 47–61 micron mesh: elution initially with methanol/methylene chloride=8:92 in volume, increasing methanol content to a final 2:8 volume ratio).

$^{13}$C NMR (75 MHz, CDCl$_3$) δ159.0, 154.6, 138.7, 129.4, 120.9, 114.5, 113.5, 88.5, 79.7, 70.9, 64.1, 63.4, 62.5, 60.8, 58.8, 54.8, 36.3, 28.8, 28.4, 26.9 ppm.

Step 2

(7R,9aS)-trans-1-[3-(octahydro-pyrido[1,2-a]pyrazin-7-ylmethoxy)-benzyl]-azetidin-3-ol dihydrochloride To a chloroform (20 ml) solution of the entire 1.48 g sample of the title compound of the previous step, diethyl ether saturated with anhydrous hydrogen chloride (25 ml) was added. The reaction was stirred at ambient temperature for 18 hours. Solvent removal in vacuo afforded the title compound (qualitative yield) as an amorphous solid.

MS m/z 332 (M+1).

Step 3

(7R,9aS)-trans-1-{3-[2-(5-fluoro-benzo[d]isoxazol-3-yl)-octahydro-pyrido[1,2-a]pyrazin-7-ylmethoxy]benzyl}-azetidin-3-ol (mixture of diastereomers)

The title compound (dihydrochloride salt) prepared in the previous step (205 mg, 0.51 mmol), 1,8-diazabicyclo[5.4.0]undec-7-ene (251 μl, 1.66 mmol), and 3-chloro-5-fluoro-benzo[d]isoxazole (110 mg, 0.64 mmol) were combined in anhydrous pyridine (250 μl). The resulting solution was heated at 90° C. for 18 hours. 10% aqueous sodium bicarbonate and methylene chloride (20 ml) of each were added, and the mixture was vigorously stirred. The aqueous phase was then extracted with three 20 ml portions of fresh methylene chloride. The combined organic extracts were dried (anhydrous sodium sulfate) and concentrated in vacuo to yield an amber oil (240 mg). Flash chromatography using the entire sample (silica gel, 47–61 micron mesh; elution with methanol/methylene chloride=1:9 in volume) afforded the (free base) title compound (40 mg, 17% yield) as a colorless amorphous solid.

MS m/z 467 (M+1).

EXAMPLE 7

(7R,9aS)-TRANS-2-(5-FLUORO-BENZO[d]ISOXAZOL-3-YL)-7-(3-MORPHOLIN-4-YLMETHYLPHENOXYMETHYL)-OCTAHYDRO-PYRIDO[1,2-a]PYRAZINE

Step 1

(7R,9aS)-trans-7-(3-morpholin-4-ylmethylphenoxymethyl)-octahydro-pyrido[1,2-a]pyrazine-2-carboxylic acid tert-butyl ester Utilizing the general procedure of Example 5, Step 3, and the product of Example 1, Step 2 (600 mg, 1.59 mmol) and substituting morpholine (419 μd, 4.77 mmol) for pyrrolidine as a reactant, the title compound was prepared as a colorless oil (354 mg, 50% yield; flash chromatography: silica gel, 47–61 micron mesh; elution with methanol/methylene chloride=4:96 in volume).

$^{13}$C NMR (100 MHz, CDCl$_3$) δ158.9, 154.5, 139.4, 129.1, 121.4, 115.1. 113.0, 79.6, 70.7, 66.9, 63.3, 60.7, 58.7, 54.7, 53.6, 36.3, 28.7, 28.4, 26.9 ppm.

MS m/z 446 (M+1).

Step 2

(7R,9aS)-trans-7-(3-morpholin-4-ylmethyl-phenoxymethyl)-octahydro-pyrido[1,2-a]pyrazine dihydrochloride Utilizing the general procedure of Example 5, Step 4, and substituting as a reactant the product of the previous step (350 mg), the title compound was prepared (dihydrochloride salt) as an amorphrous foam (quantitative yield).

Step 3

(7R,9aS)-trans-2-(5-fluoro-benzo[d]isoxazol-3-yl)-7-(3-morpholin-4-ylmethyl-phenoxymethyl)-octahydro-pyrido[1,2-a]pyrazine Utilizing the general procedure of Example 5, step 5, and substituting the product of the previous step (dihydrochloride) as a reactant (250 mg, 0.60 mmol), with appropriate scaling of other reactants/solvents, the title compound was prepared (107 mg, 37% yield) as a colorless, amorphous solid. (Flash chromatography: silica gel, 47–61 micron mesh; elution with methanol/methylene chloride=4:96 in volume).

$^{13}$C NMR (100 MHz, CDCl$_3$) δ161.5, 160.3, 160.0, 140.3, 130.0, 122.3, 118.9, 118.6, 115.9, 113.8, 112.0, 111.9, 108.1, 107.8, 71.2, 68.7, 87.4, 63.8, 60.4, 59.0, 54.4, 53.9, 48.5, 36.8, 29.1, 27.0 ppm;

MS m/z 481 (M+1).

EXAMPLE 8

(7R,9aS)-TRANS-2-(5-FLUORO-BENZO[d]ISOXAZOL-3-YL-7-(3-PYRROLIDIN-1-YLMETHYL-PHENOXYMETHYL)-OCTAHYDRO-PYRIDO[1,2-a]PYRAZINE

Step 1

(7R,9aS)-trans-[2-(5-fluoro-benzo[d]isoxazol-3-yl)-octahydro-pyrido-1,2-a]pyrazin-7-yl]-methanol (Octahydro-quinazolin-3-yl)-methanol (5.42 g, 26.2 mmol), 1,8-diazobicyclo[5.4.0]-undec-7-ene (12.9 ml, 85 mmol), and 3-chloro-5-fluoro-benzo[d]isoxazole (5.54 g, 32.3 mmol) were dissolved in pyridine (16 ml), and then heated (110° C.) with stirring for 18 hours. 10% aqueous sodium bicarbonate and methylene chloride (250 ml of each) were added, and the mixture was vigorously stirred. The aqueous phase was then re-extracted with three 100 ml portions of fresh methylene chloride. The combined organic extra were dried (anhydrous sodium sulfate) and concentrated in vacuo to an amorphous solid (4.88 g). Flash chromatography of the entire sample (silica gel, 47–61 micron mesh; elution with methanol/methylene chloride=6.94 in volume) afforded the title compound (3.46 g, 43% yield) as an amorphous solid.

MS m/z 306 (M+1).

Step 2

(7S,9aS)-trans-3-[2-(5-fluoro-benzo[d]isoxazol-3-yl)-octahydro-pyrido[1,2-a]pyrazin-7-ylmethoxy]-benzoic acid methyl ester To a solution of the title compound of the previous step (3.46 g, 11 mmol), methyl-3-hydroxybenzoate (2.58 g, 17 mmol), diethylazodicarboxylate (2.08 ml, 13.2 mmol), and triphenylphosphine (3.46 g, 13.2 mmol) were combined in tetrahydrofuran (50 ml). The solution was heated (50° C.)

and stirred for 18 hours. 10% aqueous sodium bicarbonate and methylene chloride (100 ml of each) were added, and the mixture was vigorously stirred. The aqueous phase was then re-extracted with three 50 ml portions of fresh methylene chloride. The combined organic extracts were, in turn, sequentially extracted with 1N aqueous sodium hydroxide and 10% aqueous sodium bicarbonate. The separated organic phase was dried (anhydrous sodium sulfate) and the solvent was removed in vacuo, yielding a tacky solid (12.75 g). Flash chromatography of the entire sample (silica gel, 47–61 micro mesh; elution with methanol/methylene chloride=4:96 in volume) afforded the title compound (2.90 g, 60% yield) as colorless amorphous solid.

MS m/z 440 (M+1).

Step 3

(7R,9aS)-trans-{3-[2-(5-fluoro-benzo[d]isoxazol-3-yl)-octahydro-pyrido[1,2-a]pyrazin-7-ylmethoxy]-phenyl}-methanol To a well stirred, ice bath-chilled partial solution of the title compound of the previous step (2.90 g, 6.6 mmol) in diethylether (25 ml)/tetrahydrofuran (30 ml), a 1.0M diethyl ether solution of lithium aluminum hydride (8.25 ml, 8.25 mmol) was added dropwise. The reaction mixture was then vigorously stirred at ambient for 1 hour before quenching by cautious dropwise addition (at 5–10° C.) of a total of 1 ml 1N aqueous sodium hydroxide. After stirring at ambient temperature for 30 minutes, the mixture was dried with anhydrous sodium sulfate and then filtered through celite. Solvent removal in vacuo afforded an oil (3.6 g). Flash chromatography of the entire sample (silica gel, 47–61 micron mesh; elution with methanol/methylene chloride=6:94 in volume) afforded the title compound (in free base form) as a colorless amorphous solid (1.83 g; 67% yield).

$^{13}$C NMR (75 MHz, CDCl$_3$) δ160.5, 159.2. 142.6, 129.6, 119.2, 118.2, 117.9, 113.7, 112.9, 111.4, 111.3, 107.4, 107.1, 70.9, 65.2, 60.1, 58.6, 54.1, 53.6, 48.2, 36.3, 28.9, 26.9 ppm.

MS m/z 412 (M+1).

Step 4

(7R,9aS)-trans-{3-[2-(5-fluoro-benzo[d]isoxazol-3-yl)-octahydro-pyrido[1,2-a]pyrazin-7-ylmethoxy]-phenyl}-methanol methane sulfonate To a well-stirred mixture of the title compound (440 mg, 1.07 mmol) of the previous step (partially dissolved) and triethylamine (186 μl, 1.34 mmol) in methylene chloride (10 ml), at ambient temperature, methanesulfonyl chloride (91 μl, 1.18 mmol) was added. After stirring for 20 minutes, additional portions of triethylamine (18.6 μl, 0.13 mmol) and methanesulfonyl chloride (9.1 μl, 0.12 mmol) were added. The reaction was then stirred for an additional 20 minutes before quenching with 10% aqueous sodium bicarbonate (with 20 ml of methylene chloride added). The reaction mixture was extracted with three 10 ml fresh portions of methylene chloride. The combined organic extracts were dried (anhydrous sodium sulfate) and concentrated in vacuo to afford the title compound as a viscous oil (528 mg, quantitative yield). The product was used in the next step without further purification.

MS m/z 490 (M+1).

Step 5

(7R,9aS)-trans-2-(5-fluoro-benzo[d]isoxazol-3-yl-7-(3-pyrrolidin-1-ylmethyl-phenoxymethyl)-octahydro-pyrido[1,2-a]pyrazine (free base)

A reaction mixture consisting of the mesylate title compound from the previous step (79 mg, 0.16 mmol) and pyrrolidine (42 μl, 0.48 mmol) in acetonitrile (2 ml was stirred at 55° C. for 18 hours. The solvent was removed n vacuo, and the residue was extracted into a 10% aqueous sodium bicarbonate/methylene chloride biphasic mixture (20 ml of each). The organic phase was then extracted with three 10 ml portions of fresh methylene chloride. The combined organic extracts were dried (anhydrous sodium sulfate), and then concentrated in vacuo to afford a colorless amorphous solid (100 mg). Successive pulping of the pulverized solid with two 15 ml portions of hexanes (with careful pipette siphoning off of each hexane extract after pulping) afforded the title compound as a colorless amorphous solid (60 mg, 81% yield). This product was identical in all respects to the amorphous free base title compound product of Example 5/Step 5.

EXAMPLE 9

(7R,9aS)-TRANS-2-(4-FLUORO-BENZO[d]ISOXAZOL-3-YL)-7-(3-PYRROLIDIN-1-YLMETHYL-PHENOXYMETHYL)-OCTAHYDRO-PYRIDO[1,2-a]PYRAZINE

Utilizing the general procedure of Example 5, Step 5 and the product of Example 5, Step 4 (337 mg, 0.84 mmol) and 3-chloro-4-fluoro-benzo[d]isoxazole (180 mg, 1.05 mmol) as reactants, and with appropriate scaling of other reagents/solvents, the title compound (90 mg, 23% yield) was obtained as a viscous oil. Flash chromatography: silica gel, 47–61 micron mesh; elution initially with methanol/methylene chloride—6:94 in volume, increasing methanol content to a final 1:9 volume ratio (90 mg, 23% yield).

MS m/z 465 (M+1).

EXAMPLE 10

(7S,9aS)-CIS-2-BENZO[d]ISOXAZOL-3-YL-7-(3-PYRROLIDIN-1-YLMETHYL-PHENOXYMETHYL)-OCTAHYDRO-PYRIDO-[1,2-a]PYRAZINE

Step 1

(7S,9aS)-cis-3-(2-Benzo[d]isoxazol-3-yl-octahydro-pyrido[1,2-a]pyrazin-7-ylmethoxy)-benzoic acid methyl ester To a well-stirred solution consisting of (7S,9aS)-cis-(2-Benzo[d]isoxazol-3-yl-octahydro-pyrido[1,2-a]pyrazin-7-yl)-methanol (3.40 g, 11.83 mmol), methyl-3-hydroxybenzoate (2.70 g, 17.75 mmol), and triphenylphosphine (3.70 g, 14.20 mmol), in anhydrous tetrahydrofuran (68 ml), diethylazodicarboxylate (2.24 ml, 14.20 mmol) was added. The resulting solution was heated at 50° C. for 2 hours. The solvent was removed in vacuo, and the resulting residue was extracted into a biphasic 1N aqueous sodium hydroxide (40 ml)/methylene chloride (50 ml) mixture. The aqueous phase was twice extracted with equal volume portions of fresh methylene chloride. The combined organic extracts were dried (anhydrous magnesium sulfate), and concentrated to an amber oil. An initial flash chromatography (silica gel, 70–230 micron mesh; elution with methanol/methylene chloride=1:99 in volume) afforded partially purified product (3.3 g, contaminants: hydrazine diethylcarboxylate and triphenylphosphine oxide). A second flash chromatography of the entire sample (silica gel, 230–400 micron mesh, elution with methanol/methylene chloride=1:99) afforded the purified title compound (1.37 g, 27% yield) as a colorless amorphous solid.

MS m/z 422 (M+1).

$^{13}$C NMR (75 MHz, CDCl$_3$) δ167.1, 164.0, 161.1, 159.3, 131.4, 129.5, 129.3, 122.2 (2), 121.8, 120.1, 116.2, 114.8, 110.5, 69.0, 60.4, 56.4, 54.2, 53.7, 52.2, 48.3, 33.7, 25.1, 24.7 ppm.

Step 2

(7S,9aS)-cis-[3-(2-Benzo[d]isoxazol-3-yl-octahydro-pyrido[1,2-a]pyrazin-7-ylmethoxy)-phenyl]methanol To a well-stirred, ice bath-chilled solution of the title compound of Step 1 (1.33 g, 3.16 mmol) in anhydrous tetrahydrofuran (nitrogen atmosphere), a 1.0M solution of lithium aluminum hydride (3.80 ml, 3.80 mmol) was added dropwise over 10 minutes. The reaction was stirred at 5° C. for 30 minutes, and then at ambient temperature for 1 hour. Subsequently, with ice bath chilling, the reaction was quenched by slow, dropwise addition of aqueous 1N sodium hydroxide (exotherm). After 15 minutes of stirring at ambient temperature, solid anhydrous sodium sulfate was added. The mixture was filtered through celite, and the filtrate was concentrated in vacuo to yield a colorless oil. Flash chromatography of the entire sample (silica gel, 230–400 micron mesh; elution with methanol/methylene chloride=2:98 in volume) afforded the title compound (891 mg, 72% yield) as a colorless amorphous solid.

MS m/z 394 (M+1);

$^{13}$C NMR (75 MHz CDCl$_3$) δ164.0, 161.1, 159.6, 142.5, 129.6, 129.5, 122.2 (2), 118.9, 116.2, 114.0, 112.9, 110.5, 68.8, 65.3, 60.4, 56.5, 54.2, 53.7, 48.3, 33.7, 25.1, 24.8 ppm.

Step 3

(7S,9aS)-cis-2-Benzo[d]isoxazol-3-yl-7-(3-pyrrolidin-1-ylmethyl-phenoxymethyl)-octahydro-pyrido[1,2-a]pyrazine.

Utilizing the title compound of Step 2 (300 mg, 0.76 mmol), triethylamine (0.118 ml, 0.91 mmol) methanesulfonyl chloride (0.063 ml, 0.81 mmol) as reactants and methylene chloride (6.0 ml) as solvent, the corresponding mesylate of the Step 2 product was prepared in situ using the method of Example 8, Step 4.

A one-third (by volume) portion of the in situ generated mesylate solution (approximately 0.25 mmol of mesylate) and pyrrolidine (0.064 ml, 0.76 mmol) were combined in acetonitrile (2 ml). The reaction was refluxed for 3 hours; then stirred at ambient temperature for 18 hours. The solvent was removed in vacuo, and the residue was extracted into a biphasic methylene chloride/saturated aqueous sodium bicarbonate mixture (60 ml of each). The aqueous phase was extracted with two equal volume portions of fresh methylene chloride. The combined organic extracts were dried (anhydrous sodium sulfate) and concentrated in vacuo, yielding a solid residue. Flash chromatography of the entire sample (silica gel, 47–61 micron mesh; elution with methylene chloride/methanol/concentrated aqueous ammonium hydroxide—18:1:0.04 in volume) afforded the title compound (60 mg, 54% yield) as a colorless amorphous solid.

$^{13}$C NMR (CDCl$_3$) δ164.0, 161.1, 159.3, 141.0, 129.5, 129.1, 122.2, 121.1, 116.2, 115.0, 113.2, 110.5, 68.7, 65.8, 60.8, 60.4, 56.5, 542, 53.7, 48.3, 33.8, 25.2, 24.8, 23.5 ppm.

EXAMPLE 11

(7S,9aS)-CIS-1-[3-(2-BENZO[d]ISOXAZOL-3-YL-OCTAHYDRO-PYRIDO[1,2-a]PYRAZIN-7-YLMETHOXY)-BENZYL]PYRROLIDINE-3,4-DIOL

To a well-stirred, ice bath chilled solution of the title compound of Example 10, Step 2 254 mg (0.65 mmol) in dichloromethane (5 ml), triethylamine (112 μl, 0.81 mmol) and methanesulfonyl chloride (55 μl, 0.71 mmol) were added; and the resulting mixture was stirred for 20 minutes at ambient temperature. Thin layer chromatography inspection indicated complete reaction (mesylate formation). Methylene chloride (25 ml) was added, and the mixture was then extracted with 25 ml of dilute (ca. 10%) aqueous sodium bicarbonate. The aqueous phase was then extracted with several equal volume fresh portions of methylene chloride. The combined organic extracts were concentrated in vacuo to afford the mesylate of the Example 10, step 2 product as an amorphous foam. The entire mesylate sample and trans-3,4-dihydroxy pyrrolidine (derived from D-tartaric acid 200 mg, 1.93 mmol) was dissolved in acetonitrile/N,N-dimethylformamide (5 ml and 1.5 ml, respectively). The solution was then stirred at 50° C. for 18 hours. The solvent was removed in vacuo, and the residue was extracted with 10% aqueous sodium bicarbonate/methylene chloride (20 ml of each). The separated aqueous phase was extracted with three fresh equal volume portions of methylene chloride. The combined organic extracts were dried (anhydrous sodium sulfate) and concentrated in vacuo to afford an oil (420 mg). Flash chromatography (silica gel; 47–61 micron mesh; elution with methanol/methylene chloride=9:91 in volume) afforded the free base form of the title compound as a colorless amorphous foam (110 mg; 35% yield).

EXAMPLE 12

(7S,9aS)-CIS-2-BENZO[d]ISOXAZOL-3-YL-7-(2-METHYL-5-PYRROLIDIN1-YLMETHYL-PHENOXYMETHYL)-OCTAHYDRO-PYRIDO[1,2-a]PYRAZINE

Step 1

(7S,9aS)-cis-3-(2-Benzo[d]isoxazol-3-yl-octahydro-pyrido[1,2-a]pyrazin-7-ylmethoxy)-4-methyl-benzoic acid methyl ester To a solution of (7S,9aS)-cis-(2-Benzo[d]isoxazol-3-yl-octahydro-pyrido[1,2-a]pyrazin-7-yl)-methanol (500 mg, 1.7 mmol), 3-hydroxy-4-methyl-benzoic acid methyl ester (432 mg, 2.6 mmol) and triphenylphosphine (525 mg, 2.0 mmol) in tetrahydrofuran (10 ml), diethylazodicarboxylate (315 μl, 2.0 mmol) was added. The reaction mixture was then stirred at 50° C. for 2 hours. The solvent was removed and the residue was extracted with a 10% sodium bicarbonate/methylene chloride (20 ml of each) biphasic mixture. The aqueous phase was then extracted with three 10 ml portions of fresh methylene chloride. The combined organic extracts were dried (anhydrous sodium sulfate), and concentrated in vacuo to an orange oil (2.01 g). Flash chromatography of the entire sample (silica gel, 47–61 micron mesh; elution with ethyl acetate/hexanes=2:8 in volume) afforded the title compound (267 mg, 36% yield) as an amorphous solid.

$^{13}$C NMR (75 MHz CDCl$_3$) δ167.5, 164.0, 161.2, 157.2, 132.6, 130.3, 129.4, 128.9, 122.2, 121.7, 116.2, 111.6, 110.5, 68.9, 60.5, 56.6, 54.2, 53.7, 52.0, 48.3, 33.8, 25.1, 24.8, 16.6 ppm.

MS m/z 436 (M+1).

Step 2

(7S,9aS)-cis-[3-(2-Benzo[d]isoxazol-3-yl-octahydro-pyrido[1,2-a]pyrazin-7-ylmethoxy)-4-methyl-phenyl]-methanol Utilizing the general procedure of Example 10, Step 2, the above-described Step 1 product (267 mg, 0.61 mmol) was converted to the title compound, isolated as a colorless oil (239 mg, 58% yield).

MS m/z 408 (M+1).

Step 3

(7S,9aS)-cis-2-Benzo[d]isoxazol-3-yl-7-(2-methyl-5-pyrrolidin-1-ylmethyl-phenoxymethyl)-octahydro-pyrido[1,2-a]pyrazine By the general procedure of Example 10, Step 3, the above-described Step 2 product (140 mg, 0.34 mmol) was converted Into the title compound (22 mg, 14% yield), isolated as a colorless amorphous solid.

$^{13}$C NMR (75 MHz CDCl$_3$) δ164.0, 162.0, 157.4, 130.2, 129.4, 125.5, 122.2, 120.7, 116.3, 111.9, 110.5, 68.7, 60.7, 60.5, 56.6, 54.3, 54.1, 53.7, 48.3, 33.9, 25.2, 24.8, 23.4, 16.1 ppm;

MS m/z 461 (M+1).

EXAMPLE 13

(7S,9aS)-CIS-2-BENZO[d]ISOXAZOL-3-YL-7-(3-METHOXY-5-PYRROLIDIN-1-YLMETHYL-PHENOXYMETHYL)-OCTAHYDRO-PYRIDO[1,2-a]PYRAZINE

Step 1

(7S,9aS)-cis-3-(2-Benzo[d]isoxazol-3-yl-octahydro-pyrido[1,2-a]pyrazin-7-ylmethoxy)-5-methoxy-benzoic acid methyl ester Utilizing the general procedure of Example 11, above and (7S,9aS)-cis-(2-Benzo[d]isoxazol-3-yl-octahydro-pyrido[1,2-a]pyrazin-7-yl-methanol (500 mg, 1.7 mmol), and 3-methoxy-5-hydroxy benzoic acid methyl ester (475 mg, 2.6 mmol) as reactants, the title compound was prepared and isolated as a colorless oil (363 mg, 47% yield).

MS m/z=452 (M+1).

Step 2

(7S,9aS)-cis-[3-(2-Benzo[d]isoxazol-3-yl-octahydro-pyrido[1,2-a]pyrazin-7-ylmethoxy)-5-methoxy-phenyl]-methanol Utilizing the general procedure of Example 10, Step 2, the above-described Step 1 product (363 mg, 0.8 mmol) was converted to the title compound, isolated as a colorless oil (247 mg, 73% yield).

$^{13}$C NMR (75 MHz, CDCl$_3$) δ164.0, 161.1, 161.0, 160.6, 143.5, 129.5, 122.3, 122.2, 116.2, 110.5, 105.2, 104.5, 100.2. 68.9, 65.2, 60.4, 56.4, 55.4, 54.2, 53.6, 48.2, 33.7, 30.3, 29.9, 25.1, 24.7 ppm.

MS m/z 424 (M+1).

Step 3

(7S,9aS)-cis-2-Benzo[d]isoxazol-3yl-7-(3-methoxy-5-pyrrolidin-1-ylmethyl-phenoxymethyl)-octahydro-pyrido[1,2-a]pyrazine By the general procedure of Example 10, Step 3, the above-described Step 2 product (240 mg, 0.57 mmol) as converted into the title compound (209 mg, 70% yield), isolated as a colorless oil.

$^{13}$C NMR (75 MHz, CDCl$_3$) δ164.0, 161.1, 160.7, 106.4, 141.7, 129.5, 122.2, 116.2, 110.4, 107.3, 106.7, 99.7, 68.8, 61.0, 60.4, 56.5, 55.3, 54.2, 53.7, 48.3, 33.8, 25.2. 24.8, 23.5 ppm;

MS m/z 477 (M+1).

EXAMPLE 14

(7S,9aS)-CIS-2-BENZO[d]ISOXAZOL-3-YL-7-(4-CHLORO-3-PYRROLIDIN-1-YLMETHYL-PHENOXYMETHYL)-OCTAHYDRO-PYRIDO[1,2-a]PYRAZINE

Step 1

(7S,9aS)-cis-5-(2-Benzo[d]isoxazol-3-yl-octahydro-pyrido[1,2-a]pyrazin-7-ylmethoxy)-2-chlorobenzoic acid methyl ester Utilizing the general procedure of Example 10, Step 1 above, and (7S,9aS)-cis-(2-Benzo[d]isoxazol-3-yl-octahydro-pyrido[1,2-a]pirazin-7-yl)-methanol (126 mg, 0.44 mmol) and 2-chloro-5-hydroxy-benzoic acid methyl ester (115 mg, 0.62 mmol) as reactants, the title compound was prepared and isolated as a colorless oil (690 mg; 20% yield).

MS m/z 456 (M).

Step 2

(7S,9aS)-cis-[5-(2-Benzo[d]isoxazol-3-yl-octahydro-pyrido[1,2-a]pyrazin-7-ylmethoxy)-2-chloro-phenyl]-methanol Utilizing the general procedure of Example 10, Step 2, the above-described Step 1 product (40 mg, 0.09 mmol) was converted to the title compound in quantitative yield, isolated as a colorless oil.

Step 3

(7S,9aS)-cis-2-Benzo[d]isoxazol-3-yl-7-(4-chloro-3-pyrrolidin-1-ylmethyl-phenoxymethyl)octahydro-pyrido[1,2-a]pirazine By the general procedure of Example 10, Step 3, the above-described Step 2 product (54 mg, 0.13 mmol) was converted into the title compound (6 mg, 10% yield), isolated as a colorless oil.

EXAMPLE 15

(7S,9aS)-CIS-2-BENZO[d]ISOXAZOL-3-YL-7-(4-PYRROLIDIN-1-YLMETHYL-PHENOXYMETHYL)-OCTAHYDRO-PYRIDO[1,2-a]PYRAZINE

Step 1

(7S,9aS)-cis-4-(2-Benzo[d]isoxazol-3-yl-octahydro-pyrido[1,2-a]-pyrazin-7-ylmethoxy)-benzoic acid methyl ester To a well-stirred solution consisting of (7S,9aS)-cis-(2-Benzo[d]isoxazol-3yl-octahydro-pyrido[1,2-a]pyrazin-7-yl)-methanol (3.49 g, 12.1 mmol), methyl-4-hydroxybenzoate (Aldrich Chemical Co., 2.80 g, 18.2 mmol), and triphenylphosphine (3.80 g, 14.6 mmol) in anhydrous tetrahydrofuran (70 ml), diethylazodicarboxylate (2.29 ml, 14.6 mmol) was added. After heating the solution for two hours at 50° C., the solvent was removed in vacuo. The residue was extracted into a biphasic 1N aqueous sodium hydroxide (40 ml)/methylene chloride (50 ml) mixture. The aqueous phase was twice extracted with equal volume portions of methylene chloride. The combined organic extracts were dried (anhydrous magnesium sulfate), and concentrated in vacuo, yielding an amber oil. Flash chromatography of the entire sample (silica gel, 70–230 micron mesh; elution with methanol/methylene chloride= 0.5:95.5 in volume) afforded the title compound (3.20 g, 63% yield) as a colorless amorphous solid.

MS m/z 422 (M+1);

$^{13}$C NMR (75 MHz, CDCl$_3$) δ166.9, 164.0, 163.1, 131.6, 129.5, 122.4, 122.2 (2), 116.2, 114.2, 110.5, 62.2, 60.4, 56.4. 54.2, 53.7, 51.8, 48.3, 33.7, 25.1, 24.7 ppm.

Step 2

(7S,9aS)-cis-[4-(2-Benzo[d]isoxazol-3-yl-octahydro-pyrido[1,2-a]pyrazin-7-ylmethoxy)-phenyl]-methanol To an ice bath chilled solution of the title compound from Step 1 (1.50 mg, 3.56 mmol) in anhydrous tetrahydrofuran (nitrogen atmosphere), a total of 4.30 ml (4.27 mmol) of a 1.0M solution of lithium aluminum hydride was added dropwise over 10 minutes. The reaction was stirred at 5° C. for 30 minutes, and then at ambient temperature for 1 hour. Finally, the reaction was quenched (5° C.) by cautious addition of 500 μl of 1N aqueous sodium hydroxide. Solid anhydrous sodium sulfate was added, and the mixture was filtered through celite. The filtrate was concentrated in vacuo, yielding an amorphous solid (1.36 g). Flash chromatography of the entire sample (silica gel, 230–400 micron mesh; elution with methanol/methylene chloride=2:98 in volume) afforded the title compound as a colorless amorphous solid (0.96 g, 68.6% yield).

MS m/z 394 (M+1);

$^{13}$C NMR (75 MHz, CDCl$_3$) δ164.0, 161.1, 158.9, 133.0, 129.5, 128.6, 122.2 (2), 110.5, 114.7, 116.2, 68.9, 65.1, 60.4, 56.5, 54.2, 53.7, 48.3, 33.7, 25.1, 24.7 ppm.

Step 3

(7S,9aS)-cis-2-Benzo[d]isoxazol-3-yl-7-(4-chloromethyl-phenoxymethyl)-octahydro-pyrido[1,2-a]pyrazine To an ice bath-chilled solution of the title compound of the previous step (1.00 g, 2.54 mmol) and triethylamine (442 μl, 3.17 mmol) in methylene chloride (22 ml), methanesulfonyl chloride 216 μl (2.80 mmol) was added. After 1 hour of stirring at 5° C., additional portions of triethylamine (442 μl) and methanesulfonyl chloride (216 μl) were added. TLC inspection of a reaction aliquot (silica gel plates; elution with methanol/methylene chloride=1:9 in volume, UV detection) indicated incomplete reaction. The reaction was then stirred at ambient temperature, at which time, a third addition of triethylamine (442 μl) and methanesulfonyl chloride (216 μl) was made. After 1.5 hours of stirring at ambient temperature, TLC inspection indicated complete reaction. The reaction was then vigorously stirred after addition of saturated aqueous sodium bicarbonate and methylene chloride (20 ml of each). The aqueous phase was extracted with an equal volume of fresh methylene chloride. The combined organic extracts were dried (anhydrous magnesium sulfate) and concentrated in vacuo to afford the title compound as an amorphous solid (1.85 g), used in the next step without further purification.

MS m/z 412 (M+1).

Step 4

(7S,9aS)-cis-2-Benzo[d]isoxazol-3-yl-7-(4-pyrrolidin-1-ylmethyl-phenoxymethyl)-octahydro-pyrido[1,2-a]pyrazine A solution consisting of the title compound from the previous step (50 mg, 0.12 mmol) and pyrrolidine (32.8 μl, 0.38 mmol) in acetonitrile (1.00 ml) was heated at 50° C. for 2.5 hours. The solvent was removed in vacuo, and the residue was extracted into a saturated aqueous sodium bicarbonate/methylene chloride biphasic mixture. The aqueous phase was extracted twice with equal volume portions of fresh methylene chloride. The combined organic extracts were dried (anhydrous magnesium sulfate) and concentrated in vacuo to yield an amorphous solid. Flash chromatography of the entire sample (silica gel, 230–400 micron mesh; elution with methanol/methylene chloride=5:95 in volume) afforded the title compound (35 mg, 61.4% yield) as a colorless amorphous solid.

MS m/z 447 (M+1).

Utilizing the methods of Examples 10–15, and the title compound from Example 10, Step 2 as the reactant, and utilizing the specified final step amine reactant, the title compounds of Examples 16–28 were prepared.

EXAMPLE 16

(7S ,9aS)-CIS-7-(3-AZETIDIN-1-YLMETHYL-PHENOXYMETHYL)-2-BENZO[d]ISOXAZOL-3-YL-OCTAHYDRO-PYRIDO[1,2-a]PYRAZINE

Final step amine reactant: azetidine; final step yield: 35% (colorless amorphous solid);

$^{13}$C NMR (75 MHz, CDCl$_3$) δ164.0. 161.1, 159.4. 139.9. 129.4. 129.2, 122.2. 120.7. 116.2. 114.4, 113.4, 110.5, 68.7, 64.0. 60.4, 56.5. 55.2, 54.2, 53.7, 48.3. 33.8, 25.2, 24.8. 17.7 ppm;

MS m/z 433 (M+1).

EXAMPLE 17

(7S,9aS)-CIS-[3-(2-BENZO[d]ISOXAZOL-3-YL-OCTAHYDRO-PYRIDO[1,2-a]PYRAZIN-7-YLMETHOXY)-BENZYL]-CYCLOPROPYLMETHYL-AMINE

Final step amine reactant: cyclopropylmethyl amine; final step yield: 23% (colorless oil);

$^{13}$C NMR (75 MHz, CDCl$_3$) δ164.0, 161.1, 159.4, 142.0, 129.5, 129.3, 122.2, 120.3, 116.2, 114.2, 113.2, 110.5, 68.7, 60.4, 56.5, 54.5, 54.2, 53.8, 53.7, 48.3, 33.8, 25.2, 24.8, 11.2 ppm.

EXAMPLE 18

(7S,9aS)-CIS-2-BENZO[d]ISOXAZOL-3-YL-7-[3-(2-METHOXYMETHYL-PYRROLIDIN-1-YLMETHYL)-PHENOXYMETHYL]-OCTAHYDRO-PYRIDO[1,2-a]PYRAZINE

Final step amine reactant: 2S-methoxymethyl-pyrrolidine; final step yield: 20% (colorless oil);

$^{13}$C NMR (CDCl$_3$) δ164.0, 161.1, 159.2, 141.4, 129.5, 129.0, 122.2, 121.2, 116.2, 115.3, 112.8, 110.5, 68.7, 63.1, 60.4, 59.7, 59.1, 56.5, 54.7, 54.2, 53.7, 48.3, 33.8, 28.6, 25.2, 24.8, 22.8 ppm;

MS m/z 490 (M+1).

EXAMPLE 19

(7S,9aS)-CIS-[3-(2-BENZO[d]ISOXAZOL-3-YL-OCTAHYDRO-PYRIDO[1,2-a]PYRAZIN-7-YLMETHOXY)-BENZYL]-CYCLOPROPYL-AMINE

Final step amine reactant: cyclopropylamine (Aldrich Chem. Co.); final step yield: 32% (colorless oil);

$^{13}$C NMR (75 MHz, CDCl$_3$) δ164.0, 161.4, 159.4, 142.2, 129.5, 129.3, 122.2, 120.3, 116.3, 114.4, 113.0, 110.5, 68.7, 60.4, 56.5, 54.2, 53.7, 48.3, 33.8, 30.1, 25.2, 24.8, 6.6, 6.4 ppm.

EXAMPLE 20

(7S,9aS)-CIS-2-BENZO[d]ISOXAZOL-3-YL-7-(3-PYRROLIDIN-1-YLMETHYL-PHENOXYMETHYL)-OCTAHYDRO-PYRIDO[1,2-a]PYRAZINE

Final step amine reactant: pyrrolidine; final step yield: 18% (colorless amorphous solid);

¹³C NMR (75 MHz, CDCl₃) δ164.0, 161.1, 159.3, 141.0, 129.5, 129.1, 122.2, 121.1, 116.2, 115.0, 113.2, 110.5, 68.7, 60.8, 60.4, 56.5, 54.2, 53.7, 48.3, 33.8, 25.2, 24.8, 23.5 ppm.

EXAMPLE 21

(7S,9aS)-CIS-2-BENZO[d]ISOXAZOL-3-YL-7-[3-(4-ETHYL-PIPERAZIN-1-YLMETHYL-PHENOXYMETHYL]-OCTAHYDRO-PYRIDO[1,2-a]PYRAZINE

Final step amine reactant: 1-ethyl-piperazine; final step yield: 17% (colorless amorphous solid);

¹³C NMR (75 MHz, CDCl₃) δ164.0, 161.1, 159.3, 139.8, 129.5, 129.1, 122.2, 121.4, 116.2, 115.4, 113.1, 110.5, 68.7, 63.1, 60.4, 56.5, 54.2, 53.7, 53.1, 52.8, 52.3, 48.3, 33.8, 25.2, 24.8, 12.0 ppm;

MS m/z 490 (M+1).

EXAMPLE 22

(7S,9aS)-CIS-[3-(2-BENZO[d]ISOXAZOL-3-YL-OCTAHYDRO-PYRIDO[1,2-a]PYRAZIN-7-YLMETHOXY)-BENZYL]-CYCLOHEXYL-AMINE

Final step amine reactant: cyclohexylamine; final step yield: 19% (colorless amorphous solid);

13C NMR (75 MHz, CDCl₃) δ164.0, 161.1, 159.4, 142.6, 129.4, 129.3, 122.2, 120.3, 116.2, 114.3, 113.0, 110.5, 68.7, 60.4, 56.5, 56.2, 54.2, 53.7, 51.1, 48.3, 33.8, 33.6, 26.2, 25.2, 25.0, 24.8 ppm.

EXAMPLE 23

(7S,9aS)-CIS-1-[3-(2-BENZO[d]ISOXAZOL-3-YL-OCTAHYDRO-PYRIDOL[1,2-a]PYRAZIN-7-YLMETHOXY)-BENZYL]-PYRROLIDIN-3-OL

Final step amine reactant hydroxypyrrolidine (derived by hydrogenolysis of R-(+)-1-benzyl-3-pyrrolidinol, Aldrich Chem. Co.); final step yield: 38% (colorless oil);

¹³C NMR (75 MHz, CDCl₃) δ164.0, 161.1, 159.3. 140.3, 129.5, 129.2, 122.2, 121.0, 116.2, 115.0, 113.2, 110.5. 71.3, 68.7, 63.0. 60.4, 60.3, 56.5, 54.2, 53.7, 52.4, 48.3, 35.0, 33.8, 25.2, 24.8 ppm;

MS m/z 463 (M+1).

EXAMPLE 24

(7S,9aS)-CIS-2-BENZO[d]ISOXAZOL-3-YL-7-[3-(2,5-DIMETHYL-[PYRROLIDIN-1-YLMETHYL)-PHENOXYMETHYL-OCTAHYDRO-PYRIDO[1,2-a]PYRAZINE

Final step amine reactant: 2S,5S-dimethylpyrrolidine [P. Beak, S. T. Kerrick, S. Wu, J. Chu, *J. Amer. Chem. Soc.*, 116, 3231–3239 (1994)]; final step yield: 19% (colorless oil);

¹³C NMR (75 MHz, CDCl₃) δ164.0, 161.1, 129.5, 129.0 128.8, 122.2, 121.6, 120.8, 116.2, 115.9, 115.0, 112.6, 110.5, 68.7, 60.4, 59.8, 56.5, 55.2, 54.2, 53.7, 51.8, 48.3, 33.8, 31.2, 30.9, 25.2, 24.8, 20.5, 17.0 ppm;

MS m/z 475 (M+1).

EXAMPLE 25

(7S,9aS)-cis-2-Benzo[d]isoxazol-3-yl-7-[3-(2,5-dimethyl-pyrrolidin-1-ylmethyl)-phenoxymethyl]-octahydro-pyridol[1,2-a]pyrazine Final step amine reactant 2R,5R-dimethylpyrrolidine [R. P. Short, R. M. Kennedy, S. Masamune, *J. Org. Chem.*, 54, 1755–1756 (1989)]; final step yield: 19% (colorless oil);

¹³C NMR (75 MHz, CDCl₃) δ164.0, 161.1, 159.3, 129.5, 129.1, 122.2, 121.0, 116.2, 115.2, 110.5, 68.7, 60.5, 56.5, 54.2, 53.7, 51.9, 48.3, 33.7, 30.8, 25.2, 24.8, 17.0 ppm;

MS m/z 475 (M+1).

EXAMPLE 26

(7S,9aS)-CIS-1-[3-(2-BENZO[d]ISOXAZOL-3-YL-OCTAHYDRO-PYRIDO[1,2-a]PYRAZIN-7-YLMETHOXY)-BENZYL]PYRROLIDINE-3,4-DIOL

Final step amine reactant: cis-3,4-dihydroxypyrrolidine (Aldrich Chem. Co.); final step yield: 33% (colorless oil);

¹³C NMR (75 MHz, CDCl₃) δ163.9, 161.1, 159.3, 139.5, 129.6, 129.3, 122.3, 122.2, 121.1, 116.1, 115.2, 113.4, 110.5, 70.5, 68.7, 60.5, 60.3, 56.5, 54.2, 53.6, 50.6, 48.2, 33.7, 25.1, 24.7 ppm;

MS m/z 479 (M+1).

EXAMPLE 27

(7S,9aS)-CIS-1-[3-(2-BENZO[d]ISOXAZOL-3-YL-OCTAHYDRO-PYRIDO[1,2-a]PYRAZIN-7-YLMETHOXY)-BENZYL]-PYRROLIDIN-3-OL

Final step amine reactant: hydroxypyrrolidine (derived by hydrogenolysis of S-(−)-1-benzyl-3-pyrrolidinol, Aldrich Chem. Co.); final step yield: 64% (colorless oil);

¹³C NMR (75 MHz, CDCl₃) δ164.0, 161.1, 159.3, 140.4, 129.5, 129.2, 122.2, 121.0, 116.2, 115.1, 113.2, 110.5, 71.3, 68.7, 63.0, 60.4, 60.3, 56.5, 54.2, 53.7, 53.4, 52.4, 48.3, 35.0, 33.8, 25.2, 24.8 ppm;

MS m/z 463 (M+1).

EXAMPLE 28

(7S,9aS)-CIS-[3-(2-BENZO[d]ISOXAZOL-3-YL-OCTAHYDRO-PYRIDO[1,2-a]PYRAZIN-7-YLMETHOXY)-BENZYL]ISOBUTYL-AMINE

Final step amine reactant: isobutyl amine; final step yield: 38% (colorless oil);

¹³C NMR (75 MHz, CDCl₃) δ164.0, 161.1, 159.4, 142.3, 129.5, 129.3, 122.2, 120.2, 116.2, 114.2, 113.1, 110.5, 68.7, 60.4, 57.5, 56.5, 54.2, 54.1, 53.7, 48.3, 33.8, 28.3, 25.2, 24.8, 20.7 ppm;

MS m/z 449 (M+1).

EXAMPLE 29

(7S, 9aS)-cis-2-BENZO[d]ISOXAZOL-3-YL-7-(2-MORPHOLIN-4-YLMETHYL-PHENOXYMETHYL)-OCTAHYDRO-PYRIDO[1,2-a]PYRAZINE Step 1)

(7S,9aS)-cis-2-(2-Benzo[d]isoxazol-3-yl-octahydro-pyrido[1,2-a]pyrazin-7-ylmethoxy)-benzonitrile A reaction mixture consisting of (7S,9aS)-cis-(2-benzo[d]isoxazol-3-yl-octahydro-pyrido[1,2-a]pyrazin-7-yl)-methanol (1.34 g, 4.66 mmol), 2-cyanophenol (834 mg, 7.0 mmol), triphenylphosphine (1.46 g, 5.60 mmol), and diethylazodicarboxylate (880 µl, 5.60 mmol) in tetrahydrofuran (35 ml) was stirred at 50° C. for 4 hours. The solvent was removed in vacuo, and the residue was extracted into a 1N aqueous sodium hydroxide/methylene chloride biphasic mixture (50 ml of each). The organic phase was then extracted twice with 25 ml portions of saturated aqueous sodium bicarbonate, dried (anhydrous sodium sulfate), and concentrated in vacuo to afford an oil (4.57 g). Flash chromatography of the entire sample (silica gel, 47–61 micron mesh; elution with methylene chloride/methanol= 97:3 in volume) yielded the title compound (1.34 g, 73% yield) as a colorless oil. TLC $R_f$ (silica gel plates; methanol/ methylene chloride=4:96 in volume; UV detection): 0.64; $^{13}$C NMR (75 MHz, CDCl$_3$) δ164.0, 161.1, 161.0, 134.3, 133.6, 129.5, 122.3, 122.2, 120.6, 116.6, 116.2, 112.6, 110.4, 102.0, 69.8, 60.4, 56.2, 54.2, 53.7, 48.3, 33.5, 25.1, 24.6 ppm.

Step 2)

(7S,9aS)-cis-2-(2-Benzo[d]isoxazol-3-yl-octahydro-pyrido[1,2-a]pyrazin-7-ylmethoxy)-benzylamine To a solution of the Step 1 title compound (1.34 g, 3.4 mmol) in anhydrous tetrahydrofuran (15 ml), a total volume of 10.3 ml (10.3 mmol) of a 1.0M solution of lithium aluminum hydride in tetrahydrofuran was added dropwise over 10 minutes. The reaction was stirred, first at 50° C. for 2.5 hours, and then at ambient temperature for 18 hours. With ice bath cooling, the reaction was cautiously quenched by dropwise addition of 800 μl of aqueous 1N sodium hydroxide over 20 minutes. After 20 minutes of stirring at ambient temperature, solid anhydrous sodium sulfate was added, and the mixture was filtered through celite. The filtrate was concentrated in vacuo, yielding the title compound as a colorless oil (1.0 g, 75% yield). TLC $R_f$ (silica gel plates; elution with methanol/methylene chloride=12:88 in volume; UV detection): 0.17; $^{13}$C NMR (75 MHz, CD$_3$OD) δ165.2, 162.4, 158.3, 131.7, 131.1, 129.7, 129.5, 126.0, 123.8, 121.6, 117.1, 112.6, 111.1, 69.8, 61.9, 57.4, 55.5, 54.5, 42.8, 35.2, 31.0, 26.1, 25.8 ppm.

Step 3)

(7S,9aS)-cis-2-Benzo[d]isoxazol-3-yl-7-(2-morpholin-4-ylmethyl-phenoxymethyl)-octahydro-pyrido[1,2-a]pyrazine A reaction mixture consisting of the title compound of Step 2 (300 mg, 0.76 mmol), sodium carbonate (243 mg, 2.3 mmol), and di-2-chloroethyl ether (112 μl, 0.96 mmol) was stirred at 65° C. for 18 hours. The solvent was removed in vacuo, and the residue was extracted into a biphasic 10% dilute aqueous sodium bicarbonate/methylene chloride (20 ml of each) mixture. The aqueous phase was then extracted with two 20 ml portions of methylene chloride. The combined organic extracts were dried (anhydrous sodium sulfate) and concentrated in vacuo to a residue which was only partially purified by an initial flash chromatography (12 g silica gel, 47–61 micron mesh; elution with methanol/ methylene chloride=4:96 in volume). The resulting 115 mg of solid semi-purified product was treated on a second flash chromatography column (6 g silica gel, 47–61 micron mesh; elution with methanol/methylene chloride=2:98 in volume) to afford the title compound (40 mg, 11% yield) as an amorphous colorless solid. MS m/Z 463 (M+1); $^{13}$C NMR (75 MHz, CDCl$_3$) δ164.0, 162.0, 157.5, 130.6, 129.5, 128.2, 126.0, 122.2 (2), 120.2, 111.7, 110.5, 68.8, 67.1, 60.4, 56.6, 54.3, 53.7, 53.6, 48.3, 33.9, 25.2, 24.8 ppm.

EXAMPLE 30

(7S,9aS)-CIS-2-BENZO[d]ISOXAZOL-3-YL-7-(2-PYRROLIDIN-1-YLMETHYL-PHENOXYMETHYL)-OCTAHYDRO-PYRIDOL[1,2-a]PYRAZINE

To a solution of the title compound of Example 26, Step 2 (300 mg, 0.76 mmol) in N,N-dimethylformamide (3.5 ml), sodium carbonate (243 mg, 2.3 mmol) and 1,4-dibromobutane (100 μl, 0.84 mmol) were added, and the reaction mixture was stirred at 80° C. for 18 hours. The solvent was removed in vacuo, and the residue was extracted into a 5% dilute aqueous sodium carbonate/methylene chloride (15 ml of each) biphasic mixture. The aqueous phase was then extracted with three 10 ml portions of fresh methylene chloride. The combined organic extracts were dried (anhydrous sodium sulfate), and concentrated in vacuo, yielding an oil (300 mg). Flash chromatography of the entire sample (silica gel, 47–61 micron mesh; elution with methanol/methylene chloride=1:9 in volume) afforded the title product (300 mg, 41% yield) as a colorless oil.

$^{13}$C NMR (75 MHz, CDCl$_3$) δ164.0, 161.1, 157.5, 133.4, 131.7, 129.5, 122.3, 122.1, 121.2, 117.3, 116.1, 112.3, 110.4, 69.4, 60.3, 56.5, 54.2, 53.6, 52.2, 51.1, 48.2, 33.7, 25.0, 24.9, 23.1 ppm;

MS m/z 447 (M+1).

EXAMPLE 31

(7S,9aS)-CIS-2-BENZO[d]ISOXAZOL-3-YL-7-(4-MORPHOLIN-4YLMETHYL-PHENOXYMETHYL)-OCTAHYDRO-PYRIDO[1,2-a]PYRAZINE

Step 1

(7S,9aS)-cis-4-(2-Benzo[d]isoxazol-3-yl-octahydro-pyrido[1,2-a]pyrazin-7-ylmethoxy)-benzonitrile To a solution of (7S,9aS)-cis-(2-benzo[d]isoxazol-3-yl-octahydro-pyrido[1,2-a]pyrazin-7-yl)-methanol (1.33 g, 4.6 mmol), 4-cyanophenol (828 mg, 6.9 mmol), triphenylphosphine (1.46 g, 5.6 mmol) and diethylazodicarboxylate (947 μl, 5.6 mmol) were added, and the resulting mixture was stirred at 50° C. for 5 hours. The solvent was removed in vacuo, and the residue was extracted into a 10% aqueous sodium bicarbonate/methylene chloride (30 ml of each) mixture. The aqueous phase was extracted with three 10 ml portions of fresh methylene chloride. The combined organic extracts were dried (anhydrous sodium sulfate), and concentrated in vacuo to an oil. Flash chromatography (silica gel, 47–61 micron mesh; elution with methanol/methylene chloride=1:99 in volume) afforded the title compound (quantitative yield) as an amber oil.

MS m/z 389 (M+1).

Step 2

(7S,9aS)-cis-4-(2-Benzo[d]isoxazol-3-yl-octahydro-pyrido-1,2-a]pyrazin-7-ylmethoxy)-benzylamine To a solution of the title compound from the previous step (2.9 g, 4.6 mmol) in anhydrous tetrahydrofuran (16 ml), a 1.0M solution of lithium aluminum hydride in tetrahydrofuran (13.8 ml, 13.8 mmol) was added dropwise over several minutes. The reaction mixture was then stirred at 50° C. for 4 hours. With ice bath cooling, the reaction was then quenched by dropwise addition of 1N aqueous sodium hydroxide (1 ml) over 20 minutes. After stirring at ambient temperature for 1 hour, anhydrous sodium sulfate was added. The mixture was filtered, and the filtrate was concentrated in vacuo yielding a viscous oil. The crude amine product was further purified by hydrochloride salt formation as follows: The entire sample was dissolved in ethanol/ethyl acetate (10 ml of each). An ether solution (20 ml) saturated with anhydrous hydrogen chloride was added, yielding the amine bis-hydrochloride salt as a colorless amorphous precipitate, which was filtered and dried in vacuo. The free base was liberated by dissolution of the entire sample in a 10% aqueous sodium carbonate/methylene chloride (50 ml of each) mixture. The aqueous phase was then extracted with three 5 ml portions of fresh methylene chloride. The combined organic extracts were dried (anhydrous sodium sulfate) and concentrated in vacuo to afford the title compound (730 mg) as a colorless oil.

$^{13}$C NMR (75 MHz, CD$_3$OD) δ165.2, 162.4, 160.8, 133.2, 133.0, 131.2, 130.9, 130.0, 129.6, 123.8, 117.1, 116.0, 111.1, 69.8, 61.9, 57.2, 55.4, 54.5, 44.7, 35.1, 26.0, 25.7 ppm;

MS m/z 393 (M+1).

Step 3

(7S,9aS)-cis-2-BENZO[d]ISOXAZOL-3-YL-7-(4-MORPHOLIN-4-YLMETHYL-PHENOXYMETHYL) OCTAHYDRO-PYRIDO[1,2-a]PYRAZINE To a solution of the title compound from Step 2 (175 mg, 0.45 mmol) in N,N-dimethylformamide (20 ml), sodium carbonate (142 mg, 1.33 mmol) and 2-chloroethyl ether (72 μl, 0.50 mmol) were added, and the reaction mixture was stirred at 85° C. for 18 hours. The solvent was then removed in vacuo, and the residue was extracted with a water/methylene chloride (15 ml of each) biphasic mixture. The aqueous phase was extracted with three 10 ml portions of fresh methylene chloride. The combined organic extract were dried (anhydrous sodium sulfate), and concentrated in vacuo, yielding an oil (170 mg). Flash chromatography of the entire sample (silica gel, 47–61 micron mesh; elution with methanol/methylene chloride=2.98 in volume) afforded the title compound (19 mg, 9% yield) as an oil.

$^{13}$C NMR (75 MHz, CDCl$_3$) δ164.0, 161.0, 158.6. 130.4, 129.5, 122.2, 116.0, 114.4, 110.5, 68.8, 67.02, 62.9, 60.4, 56.5, 54.2, 53.7, 53.5, 48.3, 33.7, 25.2, 24.8 ppm;

MS m/z 463 (M+1).

EXAMPLE 32

(7S,9aS)-CIS-2-BENZO[d]ISOXAZOL-3-YL-7-(4-PYRROLIDIN-1-YLMETHYL-PHENOXYMETHYL)-OCTAHYDRO-PYRIDO[1,2-a]PYRAZINE

To a solution of the title compound of Example 31, Step 2 (200 mg, 0.51 mmol) in N,N-dimethylformamide (2.5 ml), sodium carbonate (162 mg, 1.53 mmol) and 1,4-dibromobutane (67 μl, 0.56 mmol) were added, and the reaction mixture was stirred at 85° C. for 18 hours. The solvent was removed in vacuo, and the residue was extracted into a 5% dilute aqueous sodium carbonate/methylene chloride (15 ml of each) biphasic mixture. The aqueous phase was extracted with three 10 ml portions of fresh methylene chloride. The combined organic extracts were dried (anhydrous sodium sulfate) and concentrated in vacuo, yielding an oil (220 mg). Flash chromatography of the entire sample (silica gel, 47–61 micron mesh; elution with methanol/methylene chloride=6:94 in volume) afforded the title compound (22 mg, 10% yield) as an oil.

$^{13}$C NMR (75 MHz, CDCl$_3$) δ164.0, 161.0, 160.4, 135.0, 132.2, 129.5, 122.3, 122.2, 116.3, 115.3, 110.4, 68.9, 60.4, 57.8, 56.3, 54.2, 53.6, 52.6, 48.3, 33.5, 25.1, 24.7, 23.1 ppm;

MS m/z 447 (M+1).

EXAMPLE 33

(7R,9aS)-TRANS-2-(7-FLUORO-BENZO[d]ISOXAZOL-3-YL)-7-(3-PYRROLIDIN-1-YLMETHYL-PHENOXYMETHYL)-OCTAHYDRO-PYRIDO-[1,2a]PYRAZINE

Step 1

(7R,9aS)-trans-2,3-Difluoro-N'-hydroxy-N-methyl-N-{2-[2-methyl-5-(2-pyrrolidin-1-ylmethyl-phenoxymethyl)-piperidin-1-yl]-ethyl}-benzamidine Reactant 2,3-difluorobenzohydroximinoyl chloride was prepared in situ as follows: A steady stream of chlorine gas was passed for 30 minutes through a dry ice-acetone bath chilled, well-stirred, partial solution of 2,3-difluoro-benzaldehyde oxime (400 mg, 2.55 mmol) in chloroform (2.62 ml). Excess chlorine was removed by a 10 minute purge with nitrogen. A total of 254 μl (1.80 mmol) of triethylamine was then added dropwise. The reaction mixture was filtered, to afford (in the filtrate) a chloroform solution of the iminoyl chloride reactant. To an ambient temperature solution of the title compound of Example 5, Step 4 (1.51 g, 3.76 mmol and 1,8-diazabicyclo[5.4.0]-undec-7-ene (1.13 ml, 7.52 mmol) in chloroform (3.2 ml, the entire aforedescribed solution of 2,4-difluorobenzohydroximinoyl chloride was added dropwise (exotherm). After 20 minutes of stirring, the reaction was quenched by addition of 20 ml of 10% dilute aqueous sodium bicarbonate. The reaction mixture was then extracted with three successive 20 ml portions of methylene chloride. The combined organic extracts were dried (anhydrous sodium sulfate) and concentrated in vacuo to an oil (1.5 g). Flash chromatography of the entire sample (silica gel, 47–61 micron mesh; elution with methanol/methylene chloride=6:94 in volume) afforded the two (syn and anti) oxime isomers of the title compound as amorphous solids.

TLC R$_f$ of less polar isomer (246 mg, 14% yield; silica gel plates; elution with methanol/methylene chloride=6:94 in volume; UV detection: 0.39.

MS m/z 485 (M+1).

TLC of more polar isomer (164 mg, 9% yield; identical TLC conditions): 0.33; MS m/z 485 (M+1).

Step 2

(7R,9aS)-trans-2-(7-Fluoro-benzo[d]isoxazol-3-yl)-7-(3-pyrrolidin-1-ylmethyl-phenoxymethyl)-octahydro-pyrido[1,2-a]pyrazine To a well-stirred partial solution of the entire product sample from Step 1 (combined oxime isomers; 410 mg, 0.85 mmol) in tetrahydrofuran, sodium hydride (38 mg of a 60% mineral oil dispersion, 0.96 mmol of sodium hydride) was added portionwise over several minutes. Anhydrous toluene (2.22 ml) was added, and the reaction was heated at 90° C. for 18 hours. At ambient temperature, first ethanol (178 μl) and then acetic acid (33 μl) were added. After stirring for 20 minutes, water was added, and the pH was adjusted to 10 by dropwise addition of 30% aqueous ammonium hydroxide. The mixture was then extracted with three 20 ml portions of methylene chloride. The combined organic extracts were dried (anhydrous sodium sulfate) and concentrated in vacuo to afford an oil (470 mg). Flash chromatography (silica gel, 47–61 micron mesh; eluting initial with methanol/methylene chloride=6:94 in volume, increasing the methanol concentration to a final 12:88 volume ratio) afforded the title compound (180 mg, 46% yield) as a colorless amorphous solid.

MS m/z 465 (M+1).

EXAMPLE 34

(7R,9aS)-TRANS-2-(6-FLUORO-BENZO[d]
ISOXAZOL-3-YL)-7-(3-PYRROLIDIN-1-
YLMETHYL-PHENOXYMETHYL)-
OCTAHYDRO-PYRIDO[1,2-a]PYRAZINE

Step 1

(7R,9aS)-trans-2,4-Difluoro-N'-hydroxy-N-methyl-N-{2-[2-methyl-5-(3-pyrrolidin-1-ylmethyl-phenoxymethyl)-piperidin-1-yl]-ethyl}-benzamidine Reactant 2,4-difluorobenzohydroximinoyl chloride was prepared in situ in 2.2 ml of chloroform from 2,4-difluoro-benzaldehyde oxime (325 mg, 2.1 mmol) by the procedure of Example 33, Step 1 (207 μl, 1.5 mmol of triethylamine was used). As before, excess chlorine was removed by nitrogen purge. As in the previous example, the solution of 2,4-difluorobenzohydroximinoyl chloride was added dropwise to a solution of the title compound from Example 5/Step 4 (1.22 g, 3.1 mmol) and 1,8-diazabicyclo[5.4.0]-undec-7-ene (927 μl, 6.2 mmol) in chloroform (2.6 ml). Work-up as in the previous example afforded 1.12 g of an oil. Flash chromatography of the entire sample (silica gel, 47–61 micron mesh; elution with methanol/methylene chloride=1:9 in volume) afforded the two isomeric oximes as amorphous solids.

TLC $R_f$ of less polar isomer (126 mg, 12% yield; silica gel plates; elution with methanol/methylene chloride 1:9 in volume): 0.38;

MS m/z 485 (M+1).

TLC $R_f$ of more polar isomer (218 mg, 21% yield; identical TLC conditions): 0.29;

MS m/z 485 (M+1).

Step 2

(7R,9aS)-trans-2-(6-Fluoro-benzo[d]isoxazol-3-yl )-7-(3-pyrrolidin-1-ylmethyl-phenoxymethyl)-octahydro-pyrido[1,2-a]pyrazine Utilizing the entire product sample (combined oxime isomers) from Step 1 [and the following reagent/solvents: sodium hydride (30 mg of 60% mineral oil dispersion, 0.76 mmol of sodium hydride), anhydrous tetrahydrofuran (0.60 ml), and anhydrous toluene (1.75)], the title compound (103 mg, 33% yield as a colorless oil) was prepared by the general procedure of Example 33, Step 2. (Flash chromatography in the final purification: silica gel 47–61 micron mesh; initial elution with methanol/methylene chloride=6:94 in volume, increase methanol concentration to a final 1:9 volume ratio).

MS m/z 465 (M+1);

$^{13}$C NMR (75 MHz, CDCl$_3$) δ5162.0, 159.1, 129.2, 123.2. 123.0, 121.4. 114.9, 113.0, 111.5, 111.2, 97.9, 97.5, 70.9. 60.6, 60.1, 58.8, 54.2, 54.1, 53.7, 48.3, 36.4, 29.0, 26.9, 23.4 ppm.

EXAMPLE 35

(7R,9aS)-TRANS-2-(6,7-DIFLUORO-BENZO[d]
ISOXAZOL-3-YL)-7-(3-PYRROLIDIN-1-
YLMETHYL-PHENOXYMETHYL)-
OCTAHYDRO-PYRIDO[1,2-a]PYRAZINE

Step 1

(7R,9aS)-2,3,4-Trifluoro-N'-hydroxy-N-methyl-N-{2-[2-methyl-5-(3-pyrrolidin-1-ylmethyl-phenoxymetyyl)-piperidin-1-yl]-ethyl}-benzamidine By the general method in Step 1 of Examples 33 and 34, and utilizing 2,3,4-trifluoro-benzaldehyde oxime (89 mg, 0.51 mmol) as starting material, a chloroform (530 μl) of 2,3,4-trifluorobenzohydroximinoyl chloride was generated in situ. By the general Step 2 method of Examples 33 and 34, the entire sample was reacted with the Example 5/Step 4 title compound (300 mg, 0.75 mmol) in chloroform (51 μl) in the presence of 1,8-diazabicyclo[5.4.0]-undec-7-ene (223 μl ,1.5 mmol). Work-up as cited in the two previous examples and flash chromatography (silica gel, 47–61 micron mesh; elution with methanol/methylene chloride 12:88 in volume) afforded a single oxime isomer (105 mg, 41% yield) as an oil.

TLC $R_f$ (silica gel plates; elution with methanol/methylene chloride=12:88 in volume; UV detection): 0.66.

MS m/z 503 (M+1);

$^{13}$C NMR (75 MHz, CDCl$_3$) δ159.1, 148.0, 140.2, 138.1, 129.1, 125.4, 121.4, 120.0 (2), 115.0, 113.2, 112.1, 112.0, 70.9, 61.1, 60.8, 58.7, 55.0, 54.1, 53.2, 47.8, 36.3, 28.7, 26.9, 23.4 ppm.

Step 2

(7R,9aS)-trans-2-(6,7-Difluoro-benzo[d]isoxazol-3-yl)-7-(3-pyrrolidin-1-ylmethyl-phenoxymethyl)-octahydro-pyrido[1,2-a]pyrazine Utilizing the entire product sample from Step 1 [and the following reagents/solvents: sodium hydride (9.4 mg of 60% mineral oil dispersion, 0.24 mol of sodium hydride), anhydrous tetrahydrofuran (0.5 ml, and anhydrous toluene (0.6 ml)], the title compound (24 mg, 25% yield as a colorless amorphous solid) was prepared by the general procedure of Step 2, Examples 34 and 35. (Flash chromatography in the final purification: silica gel, 47–61 micron mesh; elution with methanol/methylene chloride=8:92 in volume).

TLC $R_f$ (silica gel plates, elution with methanol/methylene chloride=8:92 in volume;

UV detection): 0.28;

MS m/z 483 (M+1).

EXAMPLE 36

(7R,9aS-TRANS-2-(5-FLUORO-BENZO[d]
ISOXAZOL-3-YL)-7-(3-PYRROLIDIN-1-
YLMETHYL-PHENOXYMETHYL)-
OCTAHYDRO-PYRIDO[1,2-a]PYRAZINE

Step 1

(7S,9aS)-cis-7-hydroxymethyl-2,3,4,6,7,8,9,9a-octahydro-1H-pyrido[1,2-a]-pyrazine-bis-hydrochloride (cf. F. J. Urban, European Patent Application EP 646116, published Apr. 5, 1995).

To a well-stirred ice bath chilled slurry of (7S,9aS)-cis-7-hydroxymethyl-2-tert-butoxycarbonyl)-2,3,4,6,7,8,9,9a-octahydro-1H-pyridol[1,2-a]pyrazine (150 g, 0.56 mol) in isopropyl ether (750 ml), a solution of anhydrous hydrochloric acid (61 g) in isopropyl ether (900 ml) was added in a slow, steady stream while maintaining the temperature below 10° C. After stirring the mixture at ambient temperature for 18 hours, the colorless solid was filtered and then dried in vacuo to afford the title compound bis-hydrochloride salt (quantitative yield).

Step 2

(7S,9aS)-cis-[2-(5-fluoro-benzo[d]isoxazol-3-yl)-octahydro-pyridol[1,2-a]pyrazin-7yl]-methanol To a stirred slurry of the (bis-hydrochloride salt) product of Step 1 (5.70 g, 27.6 mmol) and 3-chloro-5-fluoro-benzo[d]isoxazole (5.83 g, 33.9 mmol) in pyridine (17 ml), 1,8-diaza-bicyclo[5.4.0]undec-7-ene (13.6 ml, 90 mmol)

was added, and the resulting reaction mixture was heated at 100° C. for 18 hours. At ambient temperature the reaction mixture was vigorously mixed with a 10% aqueous sodium bicarbonate/methylene chloride (100 ml of each) biphasic mixture. The separated aqueous phase was extracted with three 50 ml portions of fresh methylene chloride. The combined organic extracts were, in turn, extracted with an equal volume of water, and then dried (anhydrous sodium sulfate) and concentrated in vacuo to an oil. Three successive triturations of the entire sample with 50 ml portions of a 1:4 mixture of ethyl acetate:hexanes was followed by careful removal of the supernatant liquid with a pipet. Finally, traces of residual solvent were removed in vacuo to afford the title compound (3.13 g, 37% yield) as a viscous amber oil.

$^{13}$C NMR (75 MHz, CDCl$_3$) δ160. 118.2. 117.9, 111.4, 111.3. 107.1, 67.9, 60.1. 58.3. 54.1. 53.7, 48.3, 34.3, 27.0. 26.4 ppm;

MS m/z 306 (M+1).

Step 3

(7S,9aS)-cis-2-(5-fluoro-benzo[d]isoxazol-3)-yl-octahydro-pyridol[1,2-a]pyrazine-7-carboxaldehyde To a well stirred ice bath-chilled solution of the title compound of the previous step (2.0 g, 6.5 mmol) and diisopropylethylamine (4.62 ml, 26 mmol) in methylene chloride (50 ml), a slurry of pyridine-sulfur trioxide complex (3.1 g, 1.95 mmol) in dimethylsulfoxide (1.20 ml) was added portionwise at a rate that maintained the temperature just below 10° C. The reaction mixture was stirred at ambient temperature for 18 hours. Water (100 ml) was added and the biphasic mixture was vigorously stirred. The separated aqueous phase was extracted with three 50 ml portions of fresh methylene chloride. The extracts (four) were combined and, in turn, extracted with three 40 ml portions of aqueous 1N hydrochloric acid. The pH of the separated acidic aqueous phase was elevated to 10 by addition of aqueous 3N sodium hydroxide, causing precipitation of a colorless fine solid, which was isolated by filtration. The entire filter cake was dissolved in methylene chloride (350 ml), and the resulting solution was dried (anhydrous sodium sulfate). Solvent removal in vacuo afforded an oil (1.8 g). Flash chromatography of the entire sample (silica gel, 47–61 micron mesh; elution with methanol/methylene chloride= 3:97 in volume) afforded the title compound (750 mg, 38% yield) as a colorless amorphous solid.

MS m/z 304 (M+1).

Thin Layer Chromatography (TLC) R$_f$ (Analtech Uniplates: silica gel GF, 250 micron mesh; elution with methanol/methylene chloride=4:96 in volume; UV detection): 0.46.

Step 4

(7R,9aS)-trans-2-(5-fluoro-benzo-[d]isoxazol-3-yl)-octahydro-pyridol[1,2-a]pyrazin-7-carboxaldehyde To a solution of the title compound from the previous step (750 mg, 2.47 mmol) in methanol (15 ml), solid potassium carbonate (83 mg, 0.6 mmol) was added, and the resulting mixture was vigorously stirred at ambient temperature for 18 hours (thus effecting a 7S to 7R site epimerization with the Step 3 title compound). The solvent was removed in vacuo, and the residue was extracted into a water/methylene chloride biphasic mixture (50 ml of each). The separated aqueous phase was extracted with three 35 ml portions of fresh methylene chloride.

The combined organic extracts were dried (anhydrous sodium sulfate) and concentrated in vacuo to afford the title compound (602 mg, 80% yield) as an amorphous solid, used in the next step without further purification.

MS m/z 304 (M+1);

TLC R$_f$ (Identical conditions to those reported in the previous step): 0.25.

Step 5

(7R,9aS)-trans-[2-(5-fluoro-benzo[d]isoxazol-3-yl)-octahydro-pyridol[1,2-a]pyrazin-7-yl]-methanol To a well-stirred, ambient temperature solution of the title compound from the previous step (602 mg, 1.98 mmol) in methanol (15 ml), solid sodium bonohydride (75 mg, 1.98 mmol) was added portionwise over 5 minutes. The reaction mixture was stirred for 18 hours at ambient temperature, and then filtered. The filtrate was concentrated in vacuo, and the residue was extracted into a water/methylene chloride (30 ml of each) biphasic mixture. The separate aqueous phase was extracted with three 35 ml portions of fresh methylene chloride. The combined organic extracts were dried (anhydrous sodium sulfate) and then concentrated in vacuo to afford the title compound (260 mg, 43% yield) as a colorless amorphous solid, identical in all respects to the title compound product of Example 8, Step 1.

Step 6

(7R,9aS)-trans-methanesulfonic acid-2-(5fluoro-benzo[d]isoxazol-3-yl)-octahydro-pyridol[1,2a]pyrazin-7-yl-ester To a well-stirred ice bath-chilled solution of the title compound product of the previous step (250 mg, 0.82 mmol) and triethylamine (143 μl, 1.03 mmol) in methylene chloride (5 ml), methanesulfonyl chloride (70 μl, 0.90 mmol was added. The reaction mixture was stirred (5° C.) for 10 minutes. The ice cooling bath was removed, and the reaction was allowed to warm for 10 minutes before quenching by vigorous mixing with a 10% aqueous sodium bicarbonate/methylene chloride (30 ml of each) biphasic mixture. The separated aqueous phase was then extracted with three 15 ml portions of fresh methylene chloride. The combined organic extracts were dried (anhydrous sodium sulfate) and concentrated in vacuo to afford the title compound (300 mg, 95% yield) as an amorphous solid.

MS m/z 384(M+1).

Step 7

(7R,9aS)-trans-2-(5-fluoro-benzo[d]isoxazol-3-yl-7-(3-pyrrolidin-1-ylmethyl-phenoxymethyl-octahydro-pyridol[1,2-a]pyrazine To a solution of 3-(1-pyrrolidinylmethyl)-phenol[*Eur. J. Med. Chem. Chem. Ther.* 20, 6, 571–574 (1985); 139 mg, 0.78 mmol] in anhydrous N-methylpyrrolidinone (1.0 ml), sodium hydride (38 mg of a 60% mineral oil dispersion, 0.95 mmol of sodium hydride) was added portionwise over several minutes. After stirring for 10 minutes at ambient temperature, the reaction mixture was heated at 65° C. for 15 minutes. A solution of the (mesylate) title compound product from the previous step (300 mg, 0.78 mmol) in anhydrous N-methyl-pyrrolidinone (2.5 ml) was added, and the stirred reaction mixture was heated at 65° C. for 18 hours. At ambient temperature, the reaction was quenched by addition/vigorous mixing with water (50 ml). The separated aqueous phase was extracted with three 5 ml portions of methylene chloride. The combined organic extracts were, in turn, extracted with two 30 ml portions of water, and then dried (anhydrous sodium sulfate). Concentration in vacuo yielded an oil (627 mg). Three successive triturations of the entire sample with 5 ml portions of hexanes with careful pipet removal of supenatant liquid after each trituration, yielded the title compound as an amorphous colorless solid (312 mg, 86% yield), identical in all respects to the (free base) title compound of Example 5, Step 5.

EXAMPLE 37

(7R,9aS)-TRANS-3-{3-[2-(5-FLUORO-BENZO[d]ISOXAZOL-3-YL)-OCTAHYDRO-PYRIDO[1,2-a]PYRAZIN-7-YLMETHOXY]-BENZYL}-3-AZA-BICYCLO[3.2.2]NONANE

Step 1

(7R,9aS)-trans-7-[3-(3-aza-bicyclo[3.2.2]non-3-ylmethyl)-phenoxymethyl]-octahydro-pyrido[1,2a]pyrazine-2-carboxylic acid tert-butyl ester To an ice bath-chilled and stirred solution of the title compound of Example 5, Step 2 600 mg, 1.6 mmol) and triethylamine (278 µl, 1.99 mmol) in anhydrous methylene chloride, methanesulfonyl chloride (135 µl, 1.75 mmol) was added, and the resulting reaction mixture was stirred (5–10° C.) for 20 minutes before quenching by addition of 10% aqueous sodium bicarbonate/methylene chloride (20 ml of each). The aqueous phase was then extracted with three 20 ml portions of fresh methylene chloride. The combined organic extracts were dried (anhydrous sodium sulfate) and concentrated in vacuo to a residue which was dissolved in acetonitrile (10 ml). 3-Azabicyclo[3.2.2]-nonane (Aldrich Chemical Co., 597 mg, 4.78 mmol) was added, and the reaction solution was heated at 50° C. for 18 hours. The solvent was removed in vacuo, and the residue was extracted into a 10% aqueous sodium bicarbonate/methylene chloride mixture (25 ml of each). The separated aqueous phase was re-extracted with three 20 ml portions of fresh methylene chloride. The combined organic extracts were dried (anhydrous sodium sulfate) and concentrated in vacuo, affording an oil (940 mg). Flash chromatography of the entire sample (silica gel, 47–61 micron mesh; elution with methylene chloride/methanol=96:4 in volume) afforded the title compound as a colorless amorphous solid (320 mg, 42% yield).

$^{13}$C NMR (75 MHz. CDCl$_3$) δ158.8, 154.5, 142.0, 128.9, 120.8, 114.3, 112.6, 79.6, 70.6, 62.7, 62.5, 60.7, 58.7, 54.7, 36.2, 30.4, 28.6, 28.3, 26.8, 25.8, 14.4 ppm; MS m/z 484 (m+1).

Step 2

(7R,9aS)-trans-3[octahydro-pyrido[1,2-a]pyrazin-7-ylmethoxy)-benzyl]-3-aza-bicyclo[3.2.2]nonane bis-hydrochloride The title compound from the previous step (320 mg, 0.66 mmol was dissolved in chloroform 5 ml. A diethyl ether (saturated) solution (6 ml) of anhydrous hydrochloric acid was added, and the resulting solution was stirred at ambient temperature for 18 hours. The solvent was removed to afford the title compound (bis-hydrochloride salt) as a colorless amorphous foam (quantitative yield).

$^{13}$C NMR (75 MHz, CD$_3$OD) δ160.5, 132.1, 131.4, 125.5, 118.7, 117.7, 70.4, 62.3, 60.5, 57.3, 51.0, 46.3, 42.0, 35.5, 29.5, 27.0 (2), 25.4, 22.5 ppm.

Step 3

(7R,9aS)-trans-3-{3-[2-(5-fluoro-benzo[d]isoxazol-3-yl)-octahydro-pyrido[1.2-a]pyrazin-7-ylmethoxy]benzyl}-3-aza-bicyclo[3.2.2]nonane A reaction mixture consisting of the title compound from the previous step (410 mg, 0.90 mmol), 3chloro-5-fluoro-1,2-benzo[d]isoxazole (201 mg, 1.17 mmol), and 1,8-diazabicyclo[5.4.0]-undec-7-ene (442 µl, 2.92 mmol) in anhydrous pyridine (400 µl) was heated at 90° C. for 18 hours. The reaction mixture was then well-mixed with a 10% aqueous sodium bicarbonate/methylene chloride mixture (20 ml of each). The separated aqueous phase was re-extracted with three 15 ml portions of methylene chloride. The combined organic extracts were dried (anhydrous sodium sulfate) and concentrated in vacuo to an oil (415 mg). Flash chromatography (silica gel, 47–61 micron mesh; elution with methanol/methylene chloride=3:97 in volume) afforded the title compound (69 mg, 15% yield) as a colorless amorphous solid.

MS m/z 519 (M+1).

EXAMPLE 38

(7R,9aS)-TRANS-2-(5FLUORO-BENZO[d]ISOXAZOL-3-YL)7-[3-CIS-OCTAHYDRO-ISOINDOL-2-YLMETHYL)-PHENOXYMETHYL]-OCTAHYDRO-PYRIDO[1,2a]PYRAZINE

Step 1

(7R,9aS)-trans-7-[3-octahydro-isoindol-2-ylmethyl)-phenoxymethyl]-octahydro-pyrido[1,2-a]pyrazine-2-carboxylic acid tert-butyl ester To an ice bath chilled and stirred solution of the title compound of Example 5, Step 2 (600 mg, 1.6 mmol) and triethylamine (279 µl, 2.0 mmol) in anhydrous methylene chloride (10 ml), methane sulfonyl chloride (135 µl, 1.75 mmol) was added. The resulting solution was stirred at ambient temperature for 20 minutes prior to quenching by addition (with vigorous stirring) of a 10% aqueous sodium carbonate (20 ml). The separated aqueous phase was extracted with three 25 ml portions of fresh methylene chloride. The combined organic extracts were dried (anhydrous sodium sulfate) and concentrated in vacuo to afford a residue which was dissolved in acetonitrile (10 ml). Cis-octahydroisoindole [Dunet, et al., *Bull. Soc. Chim. Fr.*, 906–909 (1956); 550 mg, 4.4 mmol] was added, and the reaction solution was heated at 55° C. for 18 hours. With vigorous stirring the reaction was quenched by addition of a 10% aqueous sodium bicarbonate and methylene chloride (25 ml of each). The separated aqueous phase was extracted with three equal volume portions of fresh methylene chloride. The combined organic extracts were dried (anhydrous sodium sulfate) and concentrated in vacuo, yielding an oil (870 mg). Flash chromatography (silica gel, 47–61 micro mesh; elution with methanol/methylene chloride =7:93 in volume) afforded the title compound (290 mg, 38% yield) as a colorless oil.

MS m/z 484 (M+1).

Step 2

(7R,9aS)-trans-7-[3-cis-octahydro-isoindol-2-ylmethyl)phenoxymethyl]-octahydro-pyrido[1,2-a]pyrazine-bis-hydrochloride To a solution of the title compound (260 mg) from the previous step in chloroform (6 ml) a diethyl ether (saturated solution, 6 ml) of anhydrous hydrochloric acid was added. The reaction mixture was stirred for 18 hours at ambient temperature. Solvent/excess hydrochloric acid removal in vacuo afford the title compound as a light tan amorphous foam (quantitative yield).

MS m/z 384 (M+1, free base).

Step 3

(7R,9aS)-trans-2-(5-fluoro-benzo[d]isoxazol-3-yl)-7-[3-cis-octahydro-isoindol-2-ylmethyl-phenoxymethyl]-octahydro-pyrido[1,2-a]pyrazine The free base of the title compound from the previous step was formed by dissolution of the entire bishydrochloride sample into a 50% aqueous sodium bicarbonate/methylene chloride biphasic mixture (20 ml of each) and in vacuo solvent removal/drying of the separated organic phase. A reaction solution of the liberated free base (253 mg, 0.55 mmol), 3-chloro-5-fluoro-benzo[d]isoxazole (123 mg, 0.72 mmol), and 1,8-diazabicyclo[5.4.0]-undec-7-ene (271 µl, 1.79 mmol) in anhydrous pyridine (250 µl) was heated at 90° C. for 18 hours. The solvent was removed in vacuo, and the residue was dissolved in a 10% aqueous sodium bicarbonate/methylene chloride (40 ml of each) biphasic mixture. The separated organic phase was extracted with three 20 ml portions of fresh methylene chloride. The combined organic extracts were dried (anhydrous sodium sulfate) and concentrated in vacuo, yielding an oil (370 mg). Flash chromatography of the entire sample (silica gel, 47–61 micro mesh; elution with methanol/methylene chloride= 8:92 in volume), followed by pulping in 4 ml of ethyl acetate, afforded the title compound as a colorless amorphous solid (74 mg, 26% yield).

MS M/z 519 (M+1).

EXAMPLE 39

(7R,9aS-TRANS-2-(5-FLUORO-BENZO[d] ISOXAZOL-3-YL)-7-[3-PYRROLIDIN-1-YLMETHYL-PHENOXYMETHYL)-OCTAHYDROPYRIDO[1,2-a]PYRAZINE

Step 1

(7R,9aS)-trans-(2,5-Difluoro-phenyl)-[7-(3-pyrrolidin-1-ylmethyl-phenoxymethyl)-octahydro-pyrido[1,2-a]pyrazin-2-yl]-methanone oxime Using the procedure of Step 1 of Examples 34 and 35, and using 2,5-difluorobenzaldehyde oxime (79 mg, 0.50 mmol) as the starting material, and triethylamine (49 µl, 0.35 mmol as a base, and chloride gas as a reactant, a chloroform solution (529 µl) of 2,5-difluorobenzohydroximinoyl chloride was generated in situ, and then reacted with the title compound from Example 5 Step 4 (300 mg, 0.75 mmol) by the method of Step 2, Examples 34 and 35. 1,8-Diazabicyclo [5.4.0]-undec-7-ene (223 µl, 1.5 mmol and chloroform (635 µl ) were used, respectively, as the base and reaction solvent, and the reaction was conducted for 18 hours at ambient temperature. Work up of the reaction mixture was conducted as indicated in Examples 33, 34 and 35, and flash chromatography (silica gel, 47–61 micro mesh; elution initially with methanol/methylene chloride=8:92 in volume, increasing elution solvent polarity during the process to a final methanol/methylene chloride/concentrated aqueous ammonium hydroxide=20:79:1 mixture in volume) afforded the title compound (syn, anti-oxime mixture) as a colorless oil (90 mg, 37% yield).

MS m/z 485 (M+1).

Step 2

(7R,9as)-trans-2-(5-fluoro-benzo[d]isoxazol-3-yl)-7-[3-pyrrolidin-1-ylmethyl-phenoxymethyl)-octahydro-pyrido[1, 2-a]pyrazine The entire sample product from Step 1 (90 mg, 0.19 mmol) was stirred in anhydrous tetrahydrofuran (150 µl). Sodium hydride (17.8 mg of a 60% sodium hydride mineral oil dispersion; 44 mmol of sodium hydride), toluene (475 µl), and anhydrous dimethylformamide (500 µl) were added, and the reaction mixture was heated at 85° C. for 18 hours. Two additional portions of sodium hydride (each 8.9 mg of 60% sodium hydride mineral oil dispersion; each 22 mmol of sodium hydride) were added at the beginning and after two hours of a final four hour 85° C. reaction heating period. Ethanol (39 µl) and acetic acid (7.3 µl) were added, with stirring, to the cooled mixture. Five minutes thereafter, water (4 ml) was carefully added, and the resulting mixture was extracted with three 10 ml portions of methylene chloride. The combined organic extracts were dried (anhydrous sodium sulfate) and concentrated in vacuo to an oil (200 mg). Flash chromatography of the entire sample (silica gel 47–61 micron mesh; elution with methanol/methylene chloride=1:9 in volume) afforded the title compound (50 mg, 58% yield) as a colorless amorphous solid, identical in all respects to the title compound of Step 5, Example 5.

PREPARATION A

3-CHLORO-BENZO[d]ISOXAZOLE

This reactant is prepared by the method of H. Boshagen, *Chem. Berichte,* 100, 3326–3330(1967).

PREPARATION B

3-CHLORO-5-FLUOROBENZO[d]ISOXAZOLE

Step 1

5-Fluoro-2-hydroxy-benzoic acid ethyl ester [Buu-Hoi, et. al., *J. Org. Chem.,* 19, 1617–1619 (1954)]

To a solution of 5-fluorosalicylic acid (50 g) in absolute ethanol (500 ml), concentrated sulfuric acid (10 ml) was cautiously added. The solution was heated at 90° C. for 72 hours. The solvent was removed in vacuo, and the viscous residue was made basic (final pH=9) by portionwise addition of saturated aqueous sodium bicarbonate. The solution was then extracted with three 200 ml portions of methylene chloride. The combined organic extracts were dried (anhydrous sodium sulfate) and concentrated in vacuo to afford the title compound (quantitative yield) as a viscous colorless oil.

Step 2

5-Fluoro-2,N-dihydroxy-benzamide [A. Ostaszynski, *Bull. Acad. Pol. Sci. Ser. Sci. Chim.,* 8, 591–597 (1960)]

To a well-stirred solution of hydroxylamine hydrochloride (31.3 g 0.45 mol) in water (180 ml), a solution of sodium hydroxide (41.5 g, 1.04 mol) in water (360 ml was added. To the resulting solution, a solution of the Step 1 title compound (55.4 g, 0.30 mol) in 1,4-dioxane (180 ml) was added dropwise over 20 minutes. The reaction was stirred at ambient temperature for 18 hours. The 1,4-dioxane solvent was removed in vacuo, and the remaining aqueous solution was acidified (to pH 2) by addition of concentrated hydrochloric acid. The resulting precipitate was filtered, and the filter cake was air dried to afford the title compound (quantitative yield) as a colorless amorphous solid.

Step 3

3-Hydroxy-5-fluoro-benzo[d]isoxazole

To a vigorously refluxing solution of the title compound of Step 2 (96 g, 0.56 mol) in tetrahydrofuran (1.6 L), a tetrahydrofuran (3.2 L) solution of 1,1'-carbonyl dimidazole (183 g, 1.13 mol) was added in a slow stream over a 4 hour period. The solution was stirred while the solvent was removed by atmospheric distillation. The resulting oily residue was chilled with an ice bath. Water (650 ml was added slowly (causing considerable gas evolution), followed by slow addition of concentrated hydrochloric acid until the pH was 2. The mixture was then stirred for 18 hours, yielding a granulated colorless solid. Filtration, washing of the filter cake with water, and in vacuo drying afforded the title compound as a colorless solid (73 g; 85% yield).

$^1$H NMR (400 MHz, CDCl$_3$) delta 7.29–7.45 (m, 2H), 7.25 (m, 1H) ppm.

Step 4

3-Chloro-5-fluoro-benzo[d]isoxazole

To a mixture of the Step 3 title compound (1.68 g, 11 mmol) and phosphous oxychloride (2.46 ml, 26 mmol), pyridine (979 μl) was added. The resulting reaction mixture was heated at 100° C. for 18 hours. Cooled to ambient temperature, the mixture was cautiously added to water (15 ml). After 5 minutes of stirring, a solid precipitate formed, which was filtered. The filter cake was washed with water (5 ml and dried in vacuo, affording the title compound as a tan amorphous solid (973 mg, 52% yield).

$^1$H NMR (400 MHz, CD$_3$OD) δ7.50 (m, 2H), 7.72 (m, 1H).

What is claimed is:

1. A compound having an absolute stereochemistry of 7R, 9aS-trans or 7S,9aS-cis selected from:
(7R,9aS)-trans-1-{3-[2-(5-Fluoro-benzo[d]Isoxazol-3-yl)-octahydropyrido[1,2-a]pyrazin-7-ylmethoxy]-benzyl}-azetidin-3-ol;
(7R,9aS)-trans-2-(5-Fluoro-benzo[d]isoxazol-3-yl)-7-(3-morpholin-4-ylmethylphenoxymethyl)-octahydro-pyrido[1,2-a]pyrazine;
(7S,9aS)-cis-1-[3-(2-Benzo[d]isoxazol-3-yl-octahydro-pyrido[1,2-a]pyrazin-7-ylmethoxy)-benzyl]-azetidin-3-ol;
(7R,9aS)-trans-2-(4-Fluoro-benzo[d]isoxazol-3-yl)-7-(3-pyrrolidin-1-ylmethyl-phenoxymethyl)-octahydro-pyrido[1,2-a]pyrazine;
(7S,9aS)-cis-2-Benzo[d]isoxazol-3-yl-7-(3-pyrrolidin-1-ylmethyl-phenoxymethyl)-octahydro-pyrido-[1,2-a]pyrazine;
(7S,9aS)-cis-1-[3-(2-Benzo[d]isoxazol-3-yl-octahydro-pyrido[1,2-a]pyrazin-7-ylmethoxy)-benzyl]pyrrolidine-3,4-diol;
(7R,9aS)-trans-2-(5-Fluoro-benzo[d]isoxazol-3-yl)-7-(3-pyrrolidin-1-ylmethyl-phenoxymethyl)-octahydropyrido[1,2-a]pyrazine;
(7S,9aS)-cis-2-Benzo[d]isoxazol-3-yl-7-(2-methyl-5-pyrrolidin-1-ylmethyl-phenoxymethyl)-octahydro-pyrido[1,2-a]pyrazine;
(7S,9aS)-cis-2-Benzo[d]isoxazol-3-yl-7-(3-methoxy-5-pyrrolidin-1-ylmethyl-phenoxymethyl)-octahydro-pyrido[1,2-a]pyrazine;
(7S,9aS)-cis-2-Benzo[d]isoxazol-3-yl-7-(4-chloro-3-pyrrolidin-1-ylmethyl-phenoxymethyl)-octahydro-pyrido[1,2-a]pyrazine;
(7S,9aS)-cis-2-Benzo[d]isoxazol-3-yl-7-(4-pyrrolidin-1-ylmethyl-phenoxymethyl)-octahydro-pyrido[1,2-a]pyrazine;
(7S,9aS)-cis-7-(3-azetidin-1-ylmethyl-phenoxymethyl)-2-benzo[d]isoxazol-3-yl-octahydro-pyrido[1,2-a]pyrazine;
(7S,9aS)-cis-[3-(2-Benzo[d]isoxazol-3-yl-octahydro-pyrido[1,2-a]pyrazin-7-ylmethoxy)-benzyl]-cyclopropylmethyl-amine;
(7S,9aS)-cis-2-Benzo[d]isoxazol-3-yl-7-[3-(2-methoxymethyl-pyrrolidin-1-ylmethyl)-phenoxymethyl]-octahydro-pyrido[1,2-a]pyrazine;
(7S,9aS)-cis-[3-(2-Benzo[d]isoxazol-3-yl-octahydro-pyrido[1,2-a]pyrazin-7-ylmethoxy)-benzyl]-cyclopropyl-amine;
(7S,9aS)-cis-2-Benzo[d]isoxazol-3-yl-7-[3-(4-ethyl-piperazin-1-ylmethyl)-phenoxymethyl]-octahydro-pyrido[1,2-a]pyrazine;
(7S,9aS)-cis-[3-(2-Benzo[d]isoxazol-3-yl-octahydro-pyrido[1,2-a]pyrazin-7-ylmethoxy)-benzyl]-cyclohexyl-amine;
(7S,9aS)-cis-1-[3-(2-Benzo[d]isoxazol-3-yl-octahydro-pyrido[1,2-a]pyrazin-7-ylmethoxy)-benzyl]-pyrrolidin-3-ol;
(7S,9aS)-cis-2-Benzo[d]isoxazol-3-yl-7-[3-(2,5-dimethyl-pyrrolidin-1-ylmethyl)-phenoxymethyl-octahydro-pyrido[1,2-a]pyrazine;
(7S,9aS)-cis-[3-(2-Benzo[d]isoxazol-3-yl-octahydro-pyrido[1,2-a]pyrazin-7-ylmethoxy)-benzyl]-isobutyl-amine;
(7S,9aS)-cis-2-Benzo[d]isoxazol-3-yl-7-(2-morpholin-4-ylmethyl-phenoxymethyl)-octahydro-pyrido[1,2-a]pyrazine;
(7S,9aS)-cis-2-Benzo[d]isoxazol-3-yl-7-(2-pyrrolidin-1-ylmethyl-phenoxymethyl)-octahydro-pyrido[1,2-a]pyrazine;
(7S,9aS)-cis-2-Benzo[d]isoxazol-3-yl-7-(4-morpholin-4-ylmethyl-phenoxymethyl)-octahydro-pyrido[1,2-a]pyrazine;
(R,9aS)-trans-2-(7-Fluoro-benzo[d]isoxazol-3-yl)-7-(3-pyrrolidin-1-ylmethyl-phenoxymethyl)-octahydro-pyrido[1,2-a]pyrazine;
(7R,9aS)-trans-2-(6-Fluoro-benzo[d]isoxazol-3-yl)-7-(3-pyrrolidin-1-ylmethyl-phenoxymethyl)-octahydro-pyrido[1,2-a]pyrazine;
(7R,9aS)-trans-2-(6,7-Difluoro-benzodisoxazol-3-yl)-7-(3-pyrrolidin-1-ylmethyl-phenoxymethyl)-octahydro-pyrido[1,2-a]pyrazine;
(R,9aS)-trans-3-{3-[2-(5-Fluoro-benzo[d]isoxazol-3-yl)-octahydro-pyrido[1,2-a]pyrazin-7-ylmethoxy]-benzyl}-3-aza-bicyclo[3.2.2]nonane;
(7R,9aS)-trans-2-(5-Fluoro-benzo[d]isoxazol-3-yl)-7-[3-Cis-octahydro-isoindol-2-ylmethyl)-phenoxymethyl]-octahydro-pyrido[1,2-a]pyrazine; and
(7S,9aS)-cis-4-(2-benzo[d]isoxazol-3-yl)-octahydropyrido[1,2-a]pyrazin-7-ylmethxoybenzylamine and the pharmaceutically acceptable salts thereof.

2. A pharmaceutical composition for treating a disorder or condition selected from hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising an amount of a compound according to claim 1 that is effective in treating such disorder or condition and a pharmaceutically acceptable carrier.

3. A method for treating a disorder or condition that can be treated by modulating serotonergic neurotransmission in a mammal selected from depression, generalized anxiety disorder, obesity, and migraine in a mammal, comprising administering to a mammal in need of such treatment an amount of a compound according to claim 1 that is effective in treating such disorder or condition.

* * * * *